United States Patent
Honkanen et al.

(10) Patent No.: US 7,314,595 B2
(45) Date of Patent: Jan. 1, 2008

(54) HIGH THROUGHPUT MICROARRAY SPOTTING SYSTEM AND METHOD

(75) Inventors: Peter D. Honkanen, Lexington, MA (US); Timothy J. Woolaver, Billerica, MA (US); Eric E. McKenzie, Malden, MA (US); David P. Bradbury, Ipswich, MA (US); Mark R. Jones, Reading, MA (US)

(73) Assignee: Affymetrix, Inc., Santa Clara, CA (US)

( * ) Notice: Subject to any disclaimer, the term of this patent is extended or adjusted under 35 U.S.C. 154(b) by 913 days.

(21) Appl. No.: 10/476,603

(22) PCT Filed: May 2, 2002

(86) PCT No.: PCT/US02/13883

§ 371 (c)(1),
(2), (4) Date: Nov. 1, 2003

(87) PCT Pub. No.: WO02/089984

PCT Pub. Date: Nov. 14, 2002

(65) Prior Publication Data

US 2004/0151628 A1    Aug. 5, 2004

Related U.S. Application Data

(60) Provisional application No. 60/288,403, filed on May 3, 2001.

(51) Int. Cl.
*B01L 3/02* (2006.01)
(52) U.S. Cl. .......................... 422/63; 422/100; 422/64; 422/67
(58) Field of Classification Search ................ 422/100, 422/63–68.1; 436/43, 46, 180; 700/283
See application file for complete search history.

(56) References Cited

U.S. PATENT DOCUMENTS 5,061,639 A    10/1991    Lung et al. ................. 436/164

(Continued)

FOREIGN PATENT DOCUMENTS

EP    1 048 723    11/2000

(Continued)

OTHER PUBLICATIONS

International Search Report issued in PCT/US02/13883 dated Sep. 6, 2002 (6 pages).

*Primary Examiner*—Brian R. Gordon
(74) *Attorney, Agent, or Firm*—Philip L. McGarrigle

(57) ABSTRACT

A system is described for automatic retrieval of microplates from a carousel. The system includes an effector arm that retrieves a selected microplate from the carousel, a microplate retainer that receives the selected microplate from the effector arm, and a controller that directs the effector arm to the carousel for retrieval of the selected microplate and directs the effector arm to the microplate retainer so that it may receive the selected microplate. The carousel may revolve around a vertical axis. A system also is described for washing depositing elements used to spot biological materials on a substrate. Graphical user interfaces also are described for enabling a user to determine which microplates will be used to provide biological probe materials, and in what patterns those probe materials should be deposited on the substrate. The interfaces enable the user to place multiple fractions of biological materials on a same location on a substrate. Also described are graphical user interfaces that present a user with the options to select a first microplate having a plurality of wells, associate at least one probe material with one or more of the wells, and associate one or more locations on one or more substrates with the one or more wells.

26 Claims, 21 Drawing Sheets

U.S. PATENT DOCUMENTS

| | | | |
|---|---|---|---|
| 5,104,621 A | 4/1992 | Pfost et al. | 422/67 |
| 5,139,744 A * | 8/1992 | Kowalski | 422/67 |
| 5,158,895 A | 10/1992 | Ashihara et al. | 436/526 |
| 5,479,969 A | 1/1996 | Hardie et al. | 141/130 |
| 5,551,487 A | 9/1996 | Gordon et al. | |
| 5,843,376 A | 12/1998 | Ishihara et al. | 422/64 |
| 5,855,847 A | 1/1999 | Oonuma et al. | 422/64 |
| 5,906,795 A | 5/1999 | Nakashima et al. | 422/100 |
| 5,928,952 A | 7/1999 | Hutchins et al. | 436/50 |
| 6,093,574 A | 7/2000 | Druyor-Sanchez et al. | 436/180 |
| 6,096,561 A | 8/2000 | Tayi | 436/518 |
| 6,234,033 B1 | 5/2001 | Eipel | 73/864.25 |
| 6,255,116 B1 | 7/2001 | Leber et al. | 436/54 |
| 6,323,035 B1 | 11/2001 | Kedar et al. | 436/43 |
| 6,355,487 B2 | 3/2002 | Kowallis | 436/44 |
| 6,360,792 B1 | 3/2002 | Ganz et al. | 141/129 |
| 6,416,718 B1 | 7/2002 | Maiefski et al. | 422/103 |
| 6,428,752 B1 | 8/2002 | Montagu | 422/104 |
| 6,447,723 B1 | 9/2002 | Schermer et al. | 422/62 |
| 6,495,369 B1 * | 12/2002 | Kercso et al. | 436/47 |
| 6,556,923 B2 * | 4/2003 | Gallagher et al. | 702/23 |
| 6,673,316 B1 * | 1/2004 | Okamoto et al. | 422/63 |
| 6,722,395 B2 * | 4/2004 | Overbeck et al. | 141/1 |
| 6,730,517 B1 * | 5/2004 | Koster et al. | 436/47 |
| 6,733,968 B2 * | 5/2004 | Yamamoto et al. | 435/6 |
| 6,878,554 B1 * | 4/2005 | Schermer et al. | 436/180 |
| 6,890,760 B1 * | 5/2005 | Webb | 436/180 |
| 6,902,702 B1 * | 6/2005 | Winegarden et al. | 422/100 |
| 6,921,637 B2 * | 7/2005 | Audeh et al. | 435/6 |
| 6,955,788 B2 * | 10/2005 | Richards | 422/56 |
| 7,025,933 B2 * | 4/2006 | Ganz et al. | 422/63 |
| 7,101,508 B2 * | 9/2006 | Thompson et al. | 422/67 |
| 7,160,512 B2 * | 1/2007 | Hirota et al. | 422/100 |
| 2001/0019845 A1 * | 9/2001 | Bienert et al. | 436/181 |
| 2002/0001544 A1 * | 1/2002 | Hess et al. | 422/100 |
| 2002/0012611 A1 * | 1/2002 | Stylli et al. | 422/65 |
| 2002/0150450 A1 | 10/2002 | Bevirt et al. | |
| 2002/0176801 A1 * | 11/2002 | Giebeler et al. | 422/82.05 |
| 2003/0072683 A1 * | 4/2003 | Stewart et al. | 422/100 |

FOREIGN PATENT DOCUMENTS

| | | | |
|---|---|---|---|
| EP | 1 226 866 | 7/2002 | |
| EP | 02741687.4 | 5/2006 | |
| WO | WO 96/05488 | 2/1996 | |
| WO | WO 98/34091 | 8/1998 | |
| WO | WO 98/52047 | 11/1998 | |
| WO | WO 99/36760 | 7/1999 | 422/63 |
| WO | WO 0063705 | 10/2000 | |

* cited by examiner

FIG. 8A
FIG. 8B
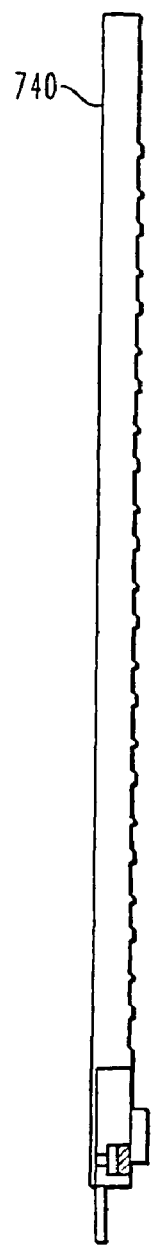
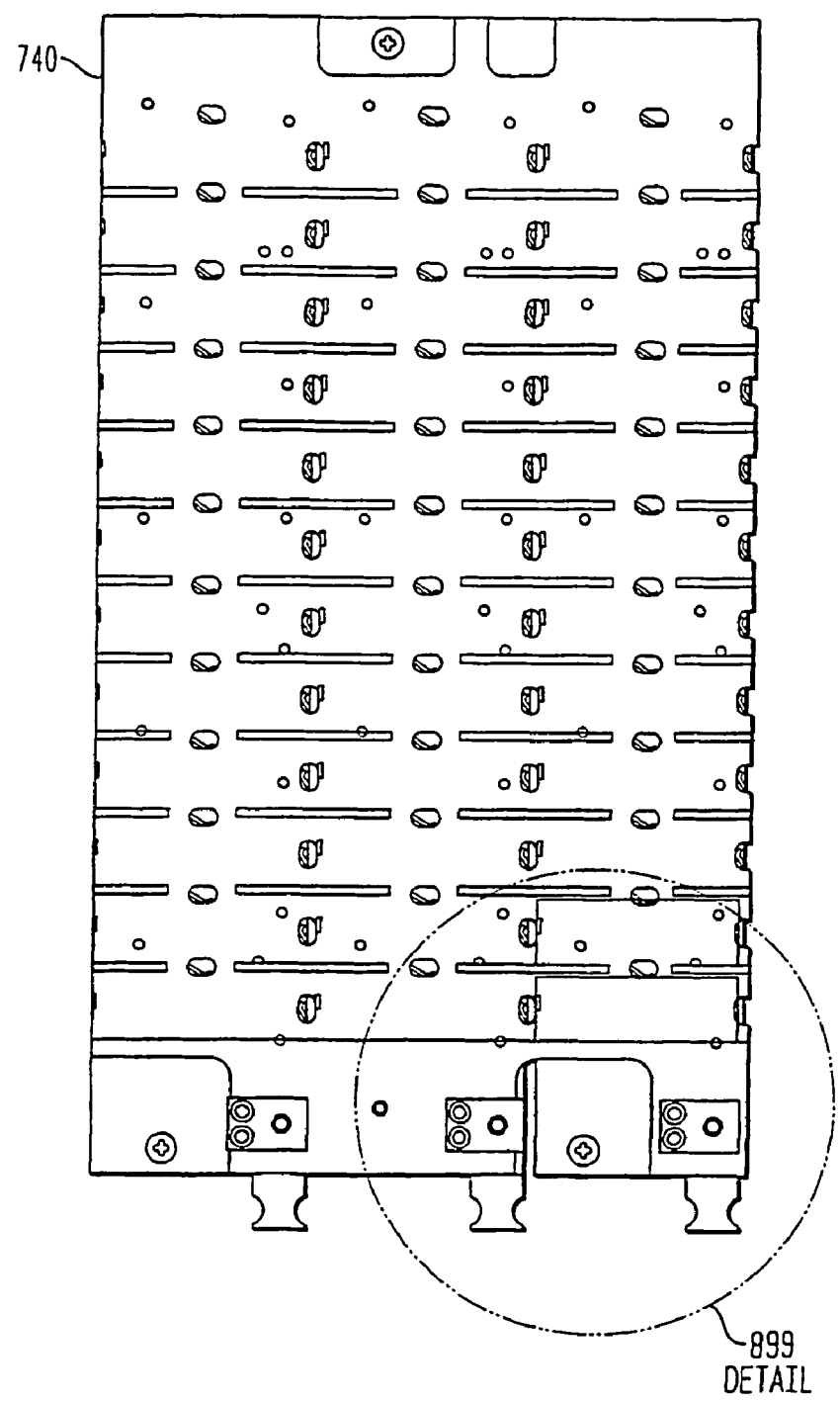
899 DETAIL

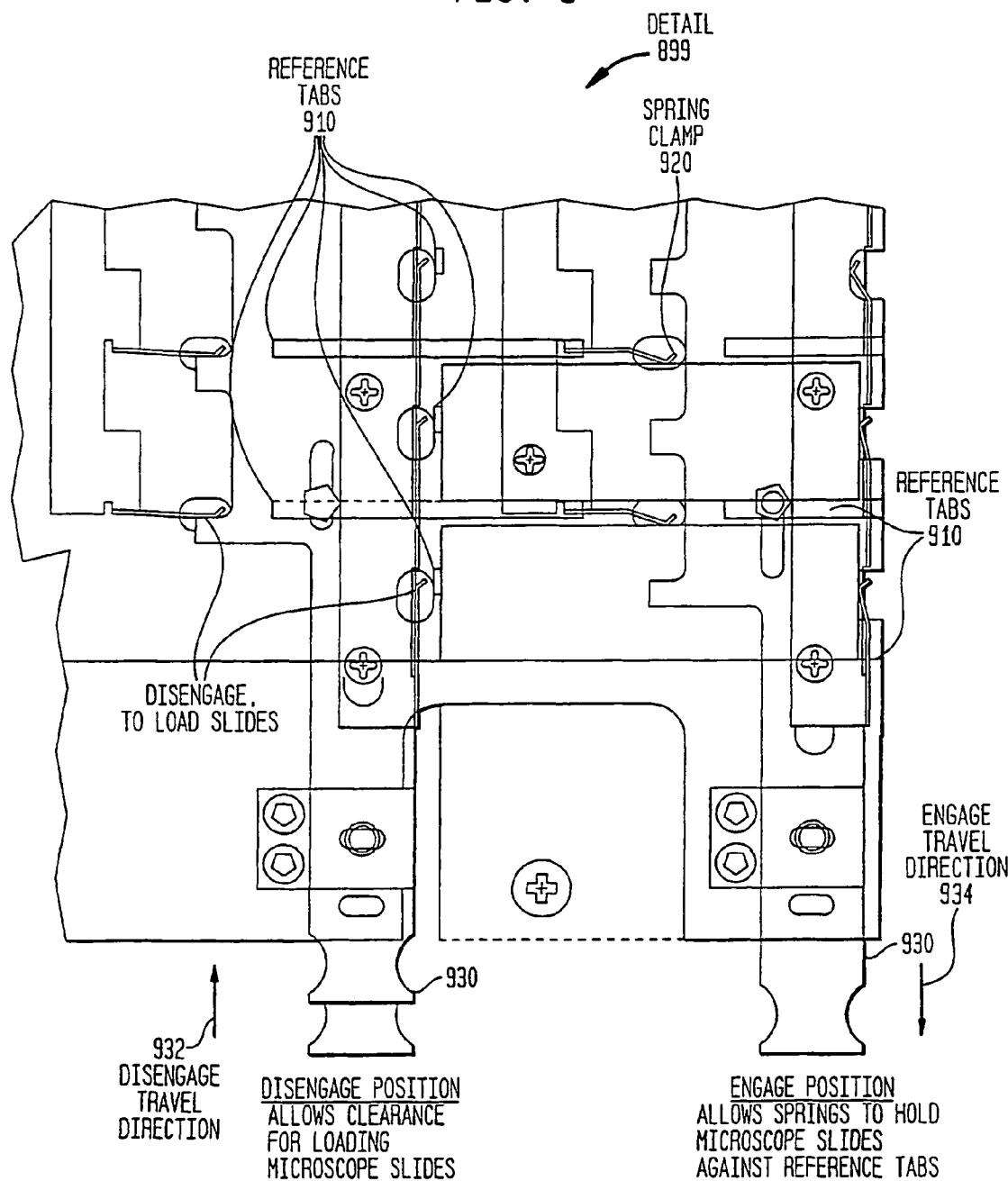

PRINTING HEAD ASSEMBLY 1020

1010 PIN AND RING

1030

1032

1030

1025 REGISTRATION C-SINK

FIG. 15A
FIG. 15B
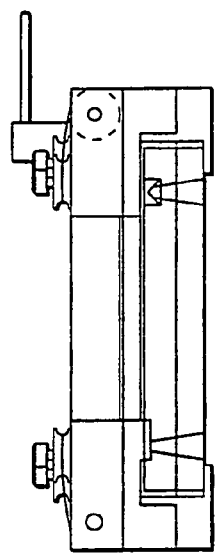
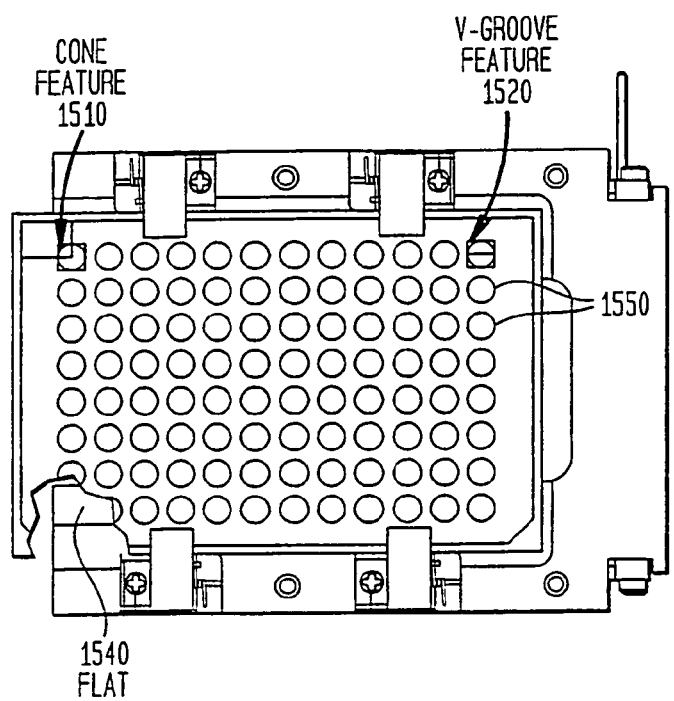
FIG. 15C
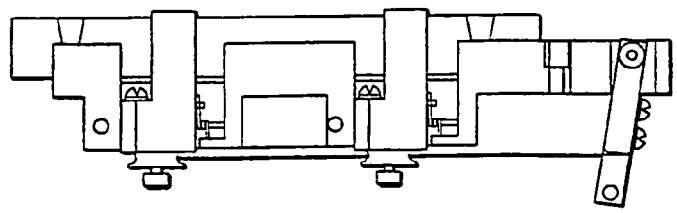

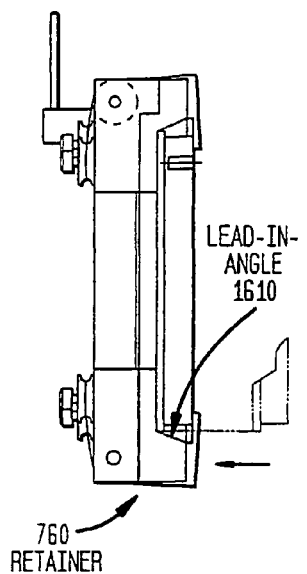 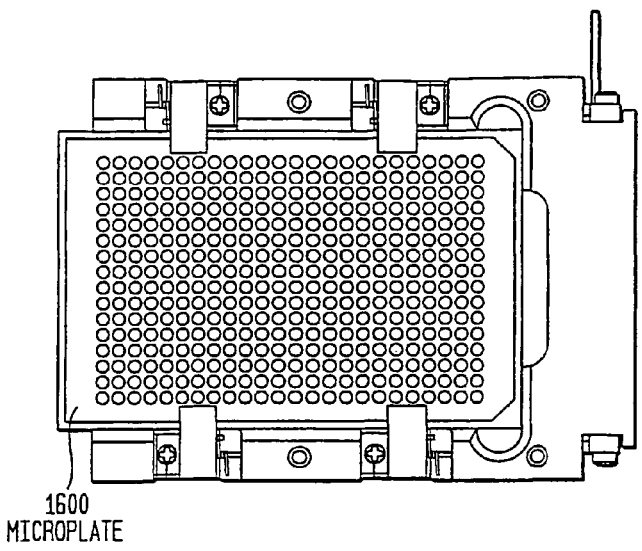
FIG. 16A  FIG. 16B
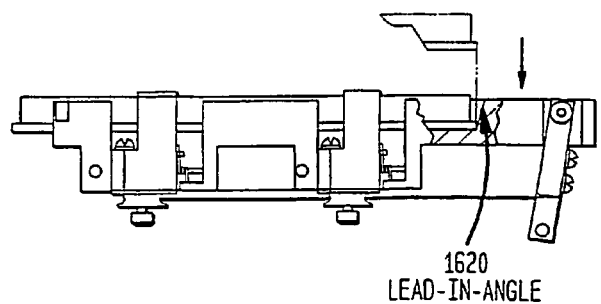
FIG. 16C

HIGH THROUGHPUT MICROARRAY SPOTTING SYSTEM AND METHOD

RELATED APPLICATIONS

This application is a National Stage of PCT Application PCT/US02/13883 filed on May 2, 2002, which claims priority from U.S. Provisional Patent Application No. 60/288,403, titled "High Throughput Microarray Spotting Device, Method, and Software Product," filed on May 3, 2001, both of which are hereby incorporated herein by reference in its entirety for all purposes.

FIELD OF THE INVENTION

The present invention relates to the deposit upon substrates of small quantities of fluid in arrays and, in particular, to spotter or arrayer devices and methods for depositing biological materials on substrates such as microscope slides.

BACKGROUND

Spotted arrays, such as those made using the Affymetrix® 417™ Arrayer from Affymetrix, Inc. of Santa Clara, Calif., are widely used to generate information about biological systems. Analysis of these data may lead to the development of new drugs and new diagnostic tools. As the uses of spotted arrays has expanded, the demand has increased for devices and methods capable of making larger numbers of spotted arrays in a reasonable time. In addition, because the spotting operation may take place over dozens of hours, there is an increased demand for greater automation of the process to reduce human interaction and to increase reliability and accuracy.

SUMMARY OF THE INVENTION

Devices and methods are described herein to address these and other needs. Reference will now be made in detail to illustrative, non-limiting, embodiments. Various other alternatives, modifications and equivalents are possible. For example, while certain systems, methods, and computer software products are described using exemplary embodiments with reference to spotted arrays made using Affymetrix® Arrayers, these systems, methods, and products are not so limited. For example, they generally may be applied with respect to many other probe arrays and parallel biological assays.

In accordance with one preferred embodiment described herein, a spotting system is described that includes a microplate holder that holds a plurality of microplates. A microplate handling apparatus of the system retrieves a first microplate having a plurality of wells from the microplate holder. One or more depositing elements receives biological material from the first microplate and deposits the biological material on one or more substrates. Also included in the system is a cleaning apparatus that washes a depositing element after it has deposited the biological material. A computer of the system has a processor and a memory unit. Stored in the memory unit are executable computer program instructions that, when executed by the processor, provide one or more graphical user interfaces that present a user with an option to select the first microplate, an option to associate at least one probe material with one or more of the plurality of wells of the first microplate, and an option to associate one or more locations on the one or more substrates with the one or more wells.

In accordance with a particular embodiment, a method is described for automatic retrieval of a plurality of well plates, each having a bottom surface and a removable lid, from a carousel. The method includes the steps of retrieving a selected well plate of the plurality of well plates from the carousel, and receiving the selected well plate from the effector arm in a well plate retainer.

In accordance with some preferred embodiments, a system is described for handling microplates holding biological materials. The system includes a carousel that holds a plurality of the microplates; an effector arm that retrieves a selected microplate from the carousel; a microplate retainer that receives the selected microplate from the effector arm; and a controller that directs the effector arm to the carousel for retrieval of the selected microplate and directs the effector arm to the microplate retainer. The selected microplate may have a plurality of wells that are capable of holding probe material such as any one or more of ligand, receptor, protein, protein fragment, peptide, nucleic acid (oligonucleotide or polynucleotide of RNA or DNA), antibody, small molecule, or other biological molecule. The carousel may be rotatable around a vertical axis. The carousel may include radially arranged segments, each having one or more slots for holding microplates. The effector arm may include a longitudinal support section that terminates with an upwardly extending tab. The longitudinal support may have a length sufficient to allow the selected microplate to rest on the support with the tab extending beyond the end of the microplate, thereby securing the microplate to the support during transfer of the microplate from the carousel to the microplate retainer. The effector arm may include one or more suction devices constructed and arranged to secure the bottom surface of the selected microplate to the effector arm at least during transfer of the microplate from the carousel to the microplate retainer or from the microplate retainer to the carousel. The effector arm further may be constructed and arranged to return the selected microplate from the microplate retainer to the carousel. The microplate transfer arm may be coupled to the effector arm and constructed and arranged to pivot, under the control of the controller, between the carousel and the microplate retainer. The microplate transfer arm further may be constructed and arranged to move the effector arm vertically to access a plurality of locations in the carousel.

In some implementations of the foregoing embodiments, the microplates include a removable lid and the effector arm further is constructed and arranged to selectively remove the lid when the microplate is received by the microplate retainer. In various aspects of these implementations, the effector arm includes one or more suction devices constructed and arranged to remove the lid from the selected microplate. The bottom surface of the selected microplate of the foregoing embodiments may include a plurality of well bottoms, each having a radius, and the microplate retainer may include one or more fiducial features for receiving the radius of well bottoms so as to register the selected microplate with respect to the microplate retainer. In these aspects, the one or more fiducial features may include at least one cone and groove fiducial feature. In these or other aspects, the microplate retainer may include one or more angled members constructed and arranged to guide the selected microplate into the microplate retainer when it receives the selected microplate from the effector arm.

In accordance with other embodiments, a method is described for handling microplates holding biological materials. The method includes the acts of rotating a plurality of microplates around a vertical axis to provide access to a selected microplate; retrieving the selected microplate; and providing the selected microplate to a microplate retainer. The selected microplate may have a plurality of wells adapted and constructed to hold probe material selected from the group consisting of any one or more of ligand, receptor, protein, protein fragment, peptide, nucleic acid (oligonucleotide or polynucleotide of RNA or DNA), antibody, small molecule, or other biological molecule. In accordance with some embodiments, a system is described for handling microplates holding biological materials. The system includes means for rotating a plurality of microplates around a vertical axis to provide access to a selected microplate; means for retrieving the selected microplate; and means for providing the selected microplate to a microplate retainer.

A system also is described in accordance with some preferred embodiments for washing one or more depositing elements used to deposit spots of biological samples. In some implementations, the system includes first and second reservoirs that are capable of holding different solutions, a washing chamber into which the depositing elements may be placed, at least one pump coupled to the reservoirs, a controller that selectively activates the first and second pumps sequentially or simultaneously, and conduits that couple one or more inlet ports of the washing chamber to the pump so that the washing solutions enter the washing chamber under the control of the controller. Thus, the depositing elements may be washed in the washing chamber by two or more different solutions, which may be applied sequentially, simultaneously, or both. Typically, the depositing elements are then moved from the washing chamber to a separate drying chamber. However, in some implementations, additional inlets may be provided to the washing chamber so that a drying agent, such as forced air or suction of air, may be applied. Fluid drying agents may also be used and, in some implementations, the two solutions may include one fluid washing solution and one fluid drying solution.

In accordance with some preferred embodiments, a system is described for washing one or more depositing elements used to deposit biological materials. The system includes a first reservoir constructed and arranged to hold a first solution; a second reservoir constructed and arranged to hold a second solution; a washing chamber constructed and arranged to receive a depositing element and having at least one inlet port and at least one drain; a first pump fluidly coupled to the first reservoir, a second pump fluidly coupled to the second reservoir; a controller coupled to the first and second pumps and constructed and arranged to selectively activate the first and second pumps sequentially or simultaneously; a first conduit fluidly coupled to the at least one inlet port and to the first pump constructed and arranged to transport the first solution to the inlet port when the controller activates the first pump; and a second conduit fluidly coupled to the at least one inlet port and to the second pump constructed and arranged to transport the second solution to the inlet port when the controller activates the second pump. The second solution may be different from the first solution. The depositing elements may include an assembly having one or more pins constructed and arranged for depositing spots of biological materials, and also having one or more rings locally associated with the pins in a one to one relationship for providing a supply of the biological materials. The first and second pumps may, in some implementations, be the same pump selectively coupled to either the first or second reservoirs. The at least one inlet port may include a first inlet port and the first and second conduits are fluidly coupled to the first inlet port through a Y-connector.

In accordance with yet other embodiments, a system is described for washing one or more depositing elements used to deposit biological materials. The system includes means for holding a first solution; means for holding a second solution; means for receiving a depositing element, wherein the receiving means includes at least one inlet port and at least one drain; and first and second pumping means for pumping the first and second solutions.

In accordance with yet another embodiment, a system is described for washing and drying one or more depositing elements used to deposit biological materials. The system includes one or more first reservoirs constructed and arranged to separately hold one or more washing agents; a second reservoir constructed and arranged to hold a drying agent; a chamber constructed and arranged to receive a depositing element and having at least one inlet port and at least one drain; a first pump coupled to the first reservoir; a second pump coupled to the second reservoir, a controller coupled to the first and second pumps and constructed and arranged to selectively activate the first and second pumps sequentially or simultaneously; a first conduit coupled to the at least one inlet port and to the first pump constructed and arranged to transport the one or more washing agents to the inlet port when the controller activates the first pump; and a second conduit coupled to the at least one inlet port and to the second pump constructed and arranged to transport the drying agent to the inlet port when the controller activates the second pump. The drying agent may include a gas, which may be air. The gas may be subject to pressure or a vacuum.

In accordance with yet a further embodiment, an arrayer system is described that includes a microplate handling apparatus that has a microplate holder that holds a plurality of microplates. The system also includes a computer that has a processor and a memory unit. The memory unit has stored therein executable computer program instructions that, when executed by the processor, performs a method comprising the steps of (a) selecting a first microplate having a plurality of wells, (b) associating at least one probe material with one or more of the wells, and (c) associating one or more locations on one or more substrates with the one or more wells. The first microplate may be held by the microplate handling apparatus. The microplate handling apparatus may further include an effector that retrieves, under control of the computer, the first microplate from the microplate holder.

Also described in accordance with another embodiment is an arrayer system that includes a microplate handling apparatus and a computer. The microplate handling apparatus has a microplate holder that holds a plurality of microplates. The computer includes a processor and a memory unit. Stored in the memory unit are executable computer program instructions that, when executed by the processor, provide one or more graphical user interfaces constructed and arranged to (a) present a user with an option to select a first microplate having a plurality of wells, (b) present a user with an option to associate at least one probe material with one or more of the wells, and (c) present a user with an option to associate one or more locations on one or more substrates with the one or more wells.

The above implementations are not necessarily inclusive or exclusive of each other and may be combined in any manner that is non-conflicting and otherwise possible, whether they be presented in association with a same, or a different, aspect or implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures or method steps and the leftmost digit of a reference numeral indicates the number of the figure in which the referenced element first appears (for example, the element 150 appears first in FIG. 1). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

FIGS. 8A-8E are schematic representations in related views of one embodiment of a platen of the arrayer of FIG. 7 including holding assemblies for securing and registering multiple slides to the platen;

FIG. 9 is a simplified schematic representation of a detail of FIG. 8;

FIGS. 15A-C are simplified schematic representation in three views of one embodiment of fiducial features for registering a bottom surface of microplates to a well plate retainer, such as may be included in the arrayer of FIG. 7;

FIGS. 16A-C are simplified schematic representation in three views of another embodiment of fiducial features for registering a bottom surface of microplates to a well plate retainer, such as may be included in the arrayer of FIG. 7;

DETAILED DESCRIPTION

Figure 1:
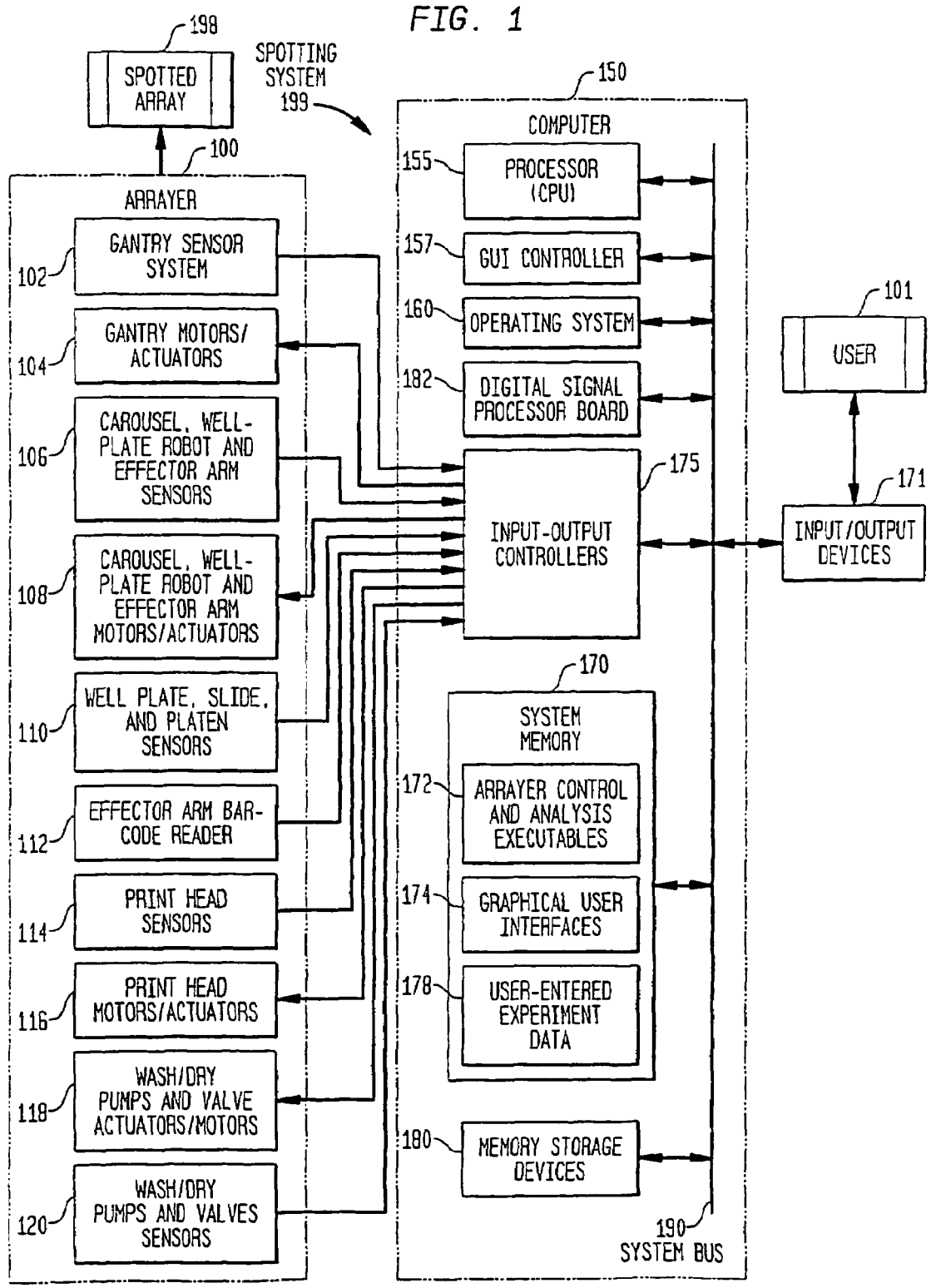
FIG. 1 is a functional block diagram of one embodiment of a system for generating spotted probe arrays including an illustrative implementation of an arrayer and an illustrative implementation of a computer for controlling the arrayer, receiving information from the arrayer, providing user interfaces, and performing analysis and data processing operations related to the generation of spotted arrays.

As noted, techniques exist for depositing or positioning pre-synthesized or pre-selected probes on or within a substrate or support. For convenience, arrays made in accordance with these techniques, or depositing/positioning techniques that may be developed in the future, are hereafter referred to as "spotted arrays." Typically, spotted arrays (such as represented schematically by spotted array 198 of FIG. 1) are fabricated on microscope slides. These arrays typically consist of liquid spots containing biological material of potentially varying compositions and concentrations. For instance, a spot in the array may include a few strands of short oligonucleotides in a water solution, or it may include a high concentration of long strands of complex proteins. Thus, numerous types of materials may be arrayed using the systems and methods described herein. As additional non-limiting examples, the spots (also referred to as "probes" of the resulting probe array) may include cells, proteins, nucleic acid sequences representing genes or EST's, or other biological elements. More specifically, the probes may be a ligand, receptor, peptide, nucleic acid (oligonucleotide or polynucleotide of RNA or DNA), protein fragment, small molecule, or any other of the biological molecules listed in U.S. Pat. No. 5,445,934 (hereby incorporated by reference herein in its entirety for all purposes) at column 5, line 66 to column 7, line 51. Thus, as a non-limiting example, a probe may refer to a nucleic acid, such as an oligonucleotide, capable of binding to a nucleic acid of complementary sequence through one or more types of chemical bonds, usually through complementary base pairing, usually through hydrogen bond formation. A probe may include natural (i.e. A, G, U, C, or T) or modified bases (7-deazaguanosine, inosine, etc.). In addition, the bases in probes may be joined by a linkage other than a phosphodiester bond, so long as the bond does not interfere with hybridization. Thus, probes may be peptide nucleic acids in which the constituent bases are joined by peptide bonds rather than phosphodiester linkages. Other examples of probes include antibodies used to detect peptides or other molecules, or any ligands for detecting its binding partners. When referring to probes (or targets, described below) as nucleic acids, it should be understood that these are illustrative examples that are not to limit the invention in any way.

The Affymetrix® 417™, 427™ and 437™ Arrayers are devices that deposit densely packed arrays of biological material on a microscope slide in accordance with aspects of these techniques. Aspects of these, and other, spot arrayers are described in U.S. Pat. Nos. 6,040,193 and 6,136,269, in PCT Applications Nos. PCT/US99/00730 (International Publication Number WO 99/36760) and PCT/US 01/04285, and in U.S. patent applications Ser. Nos. 09/501,099 and 09/122,216, all of which are hereby incorporated by reference in their entireties for all purposes. Other techniques for depositing or positioning biological probes on a substrate also exist. For example, U.S. Pat. No. 6,040,193 to Winkler, et al. is directed to processes for dispensing drops of biological material. The '193 patent, and U.S. Pat. No. 5,885,837 to Winkler, also describe separating reactive regions of a substrate from each other by inert regions and spotting on the reactive regions. The '193 and '837 patents are hereby incorporated by reference in their entireties. Other techniques are based on ejecting jets of biological material. Other implementations of the jetting technique may use devices such as syringes or piezo electric pumps to propel the biological material.

Spotted arrays typically are used in conjunction with tagged biological samples such as cells, proteins, genes or EST's, other DNA sequences, or other biological elements. These samples, referred to herein as "targets," may be processed in some implementations based on their spatial association with certain probes in the probe array. For example, one or more chemically tagged biological samples, i.e., the targets, are distributed over the probe array in a typical implementation. Some targets hybridize with at least partially complementary probes and remain at the probe locations, while non-hybridized targets are washed away. These hybridized targets, with their "tags" or "labels," are thus spatially associated with the targets' complementary probes. The hybridized probe and target may sometimes be referred to as a "probe-target pair." Detection of these pairs can serve a variety of purposes, such as to determine whether a target nucleic acid has a nucleotide sequence identical to or different from a specific reference sequence. See, for example, U.S. Pat. No. 5,837,832 to Chee, et al. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The '832, '992, '138, and '092 patents, and publication WO99/05323, are incorporated by reference herein in their entirety for all purposes.

To ensure proper interpretation of the term "probe" as used herein, it is noted that contradictory conventions exist in the relevant literature. The word "probe" is used in some contexts to refer not to the biological material that is deposited on a substrate, as described above, but to what has been referred to herein as the "target." To avoid confusion, the term "probe" is used herein to refer to probes such as those deposited to create spotted arrays.

FIGS. 1-17 illustrate non-limiting embodiments implemented generally as a system for spotting biological materials onto microscope slides. It will be understood, however, that many variations to the described implementations are possible: as just one example, the materials may be spotted onto substrates other than glass slides. For example, see U.S. Pat. Nos. 6,329,143; 6,310,189; 6,309,831; 6,197,506; and 5,744,305, all of which are hereby incorporated by reference herein in their entireties for all purposes. FIG. 1 is a simplified functional block diagram of one preferred embodiment of a spotting system, referred to as system 199 and including arrayer 100 and computer 150. In the implementation illustrated in FIG. 1, an arrayer 100 is shown in communication with computer 150 that provides various control and analysis features described herein. Computer 150 may be located locally to arrayer 100, or it may be coupled to arrayer 100 over a local-area, wide-area, or other network, including an intranet and/or the Internet (not shown). Computer 150, or any functional components of it, may also or in addition be integral to arrayer 100 in some implementations so that, for example, they are located within the same housing.

Computer 150: Computer 150 may be a personal computer, a workstation, a server, a microcomputer, or any other type of computing platform now available or that may be developed in the future. Computer 150 may include a process controller for performing control and analysis functions with respect to arrayer 100, which may be implemented in software, hardware or firmware (such as on digital signal processing board 182), or any combination thereof. Typically, computer 150 also includes known components such as processor (CPU) 155, operating system 160, system memory 170, memory storage devices 180, GUI controller 157, and input-output controllers 175, all of which typically communicate in accordance with known techniques such as via system bus 190. A user 101 may communicate with computer 150 via any of numerous conventional input and output devices 171, which typically include a display screen on which GUI's 174 generated under the control of GUI controller 157 may be displayed. Although reference will be made herein to the singular term "a user," this term is used broadly to include in some implementations plural individuals and/or machines who or that may provide input or receive output. In the illustrated implementation, computer 150 also includes digital signal processor (DSP) board 182, which may be any of a variety of PC-based DSP controller boards, such as the M44 DSP Board made by Innovative Integration of Simi Valley, Calif.

It will be understood by those skilled in the relevant art that there are many possible configurations of the components of computer 150 and that some components that may typically be included in computer 150 are not shown, such as cache memory, a data backup unit, and many other devices. Processor 155 may be a commercially available processor such as a Pentium® processor made by Intel Corporation, a SPARC® processor made by Sun Microsystems, or it may be one of other processors that are or will become available. Processor 155 executes operating system 160 that may be, for example, a Windows®-type operating system from the Microsoft Corporation; a Unix® or Linux-type operating system available from many vendors; another or a future operating system; or some combination thereof Operating system 160 interfaces with firmware and hardware in a well-known manner, and facilitates processor 155 in coordinating and executing the functions of various computer programs, such as executables 172, that may be written in a variety of programming languages. Operating system 160, typically in cooperation with processor 155, coordinates and executes functions of the other components of computer 150. Operating system 160 also provides scheduling, input-output control, file and data management, memory management, and communication control and related services, all in accordance with known techniques.

System memory 170 may be any of a variety of known or future memory storage devices. Examples include any commonly available random access memory (RAM), magnetic medium such as a resident hard disk or tape, an optical medium such as a read and write compact disc, or other memory storage device. Memory storage devices 180 may be any of a variety of known or future devices, including a compact disk drive, a tape drive, a removable or internal hard disk drive, or a diskette drive. Such types of memory storage devices 180 typically read from, and/or write to, a program storage medium (not shown) such as, respectively, a compact disk, magnetic tape, removable or internal hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory 170 and/or the program storage medium used in conjunction with memory storage devices 180.

In some embodiments, a computer program product is described comprising a computer usable medium having control logic (computer software program, including program code) stored therein. The control logic, when executed by processor 155, causes processor 155 to perform the functions of executables 172 and other software applications described herein. In other embodiments, some functions may be implemented primarily in hardware using, for example, a hardware state machine. Implementation of the hardware state machine so as to perform the functions of executables 172 described herein will be apparent to those skilled in the relevant arts.

Input-output controllers 175 could include any of a variety of known devices for accepting and processing information from a user, whether a human or a machine, whether local or remote. Such devices, as represented by input/output devices 171, include for example modem cards, network interface cards, sound cards, or other types of controllers for any of a variety of known input devices. Output controllers of input-output controllers 175 could include controllers for any of a variety of known display devices for presenting information to a user, whether a human or a machine, whether local or remote. If one of these display devices provides visual information, this information typically may be logically and/or physically organized as an array of picture elements, sometimes referred to as pixels. Graphical user interface (GUI) controller 157 may comprise any of a variety of known or future software programs for providing graphical input and output interfaces between computer 150 and a user (e.g., an experimenter wishing to use arrayer 100 to generate spotted arrays), and for processing inputs from the user (hereafter sometimes referred to as user inputs or user selections). As noted, the functional elements of computer 150 communicate with each other via system bus 204 in the illustrated embodiment. Some of these communications may be accomplished in alternative embodiments using network or other types of remote communications, such as when the functions of one or more of executables 172 are distributed over or among others of user computers and/or server computers.

Executables 172: As will be evident to those skilled in the relevant art, executables 172, if implemented in software, may be loaded into system memory 170 and/or memory storage device 180 through an input device. All or portions of executables 172 may also reside in a read-only memory or similar device of memory storage device 180, such devices not requiring that executables 172 first be loaded through input devices. It will be understood by those skilled in the relevant art that executables 172, or portions of any of them, may be transferred by processor 155 in a known manner among system memory 170, memory storage device 180, or cache memory (not shown) as advantageous for execution. Thus, applications and data structures may be shown for convenience in the illustrated embodiment as located in system memory 170 but, in some implementations, may be located in or shifted among other memory devices as convenient for data storage, data retrieval, and/or execution.

Arrayer control and analysis executables 172 represent compiled software programs or applications that, when executed in coordination with processor 155, operating system 160, and/or DSP board 182, perform various control and analysis functions. Executables 172 also perform user interface functions, typically in coordination with GUI controller 157, including creation, modification, retrieval, and data transfer operations implemented in part by the use of graphical user interfaces 174, aspects of which are shown in FIGS. 2A and 3 through 6.

Figure 2A:
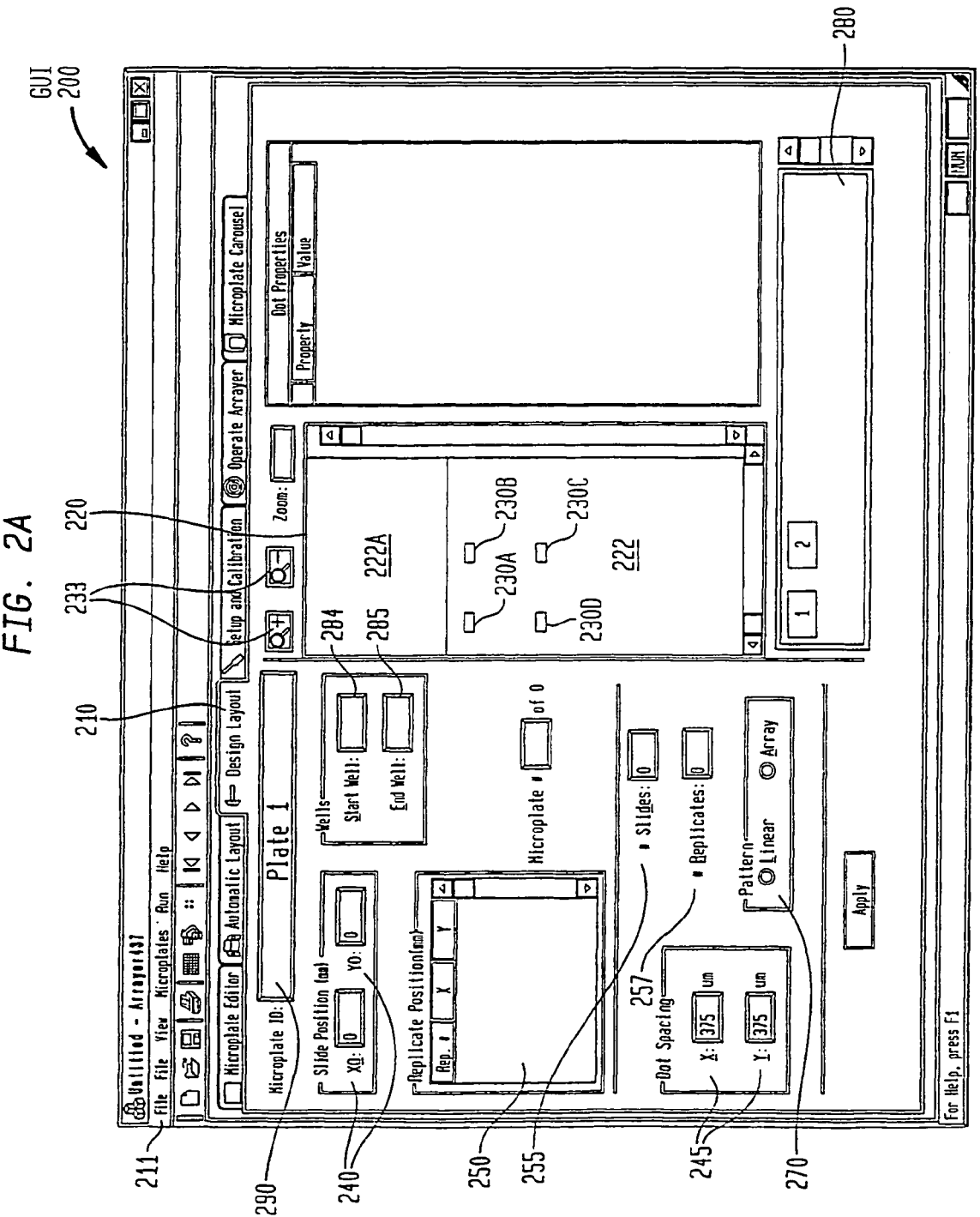
FIG. 2A is a representation of one illustrative graphical user interface generated and maintained by the computer of FIG. 1 and suitable for allowing a user to specify placement of probes on one or more substrates.

For example, with reference to illustrative implementations, in one step a user may lay out 96-well, 384-well, or other configurations of well plates with probes. FIG. 2A is a graphical representation of one of numerous graphical user interfaces (e.g., one of GUI's 174) that may be employed to enable user 101 to carry out this function. As shown in FIG. 2A, the user may select design layout tab 210 in accordance with conventional techniques so that GUI 200 is displayed. Microplate ID pane 290 displays a unique name for a microplate from which probes will be spotted onto a probe array. User 101 may select a particular microplate by specifying one from a drop down list from "File" menu item 211, or in accordance with any of a variety of other conventional techniques. In the illustrated example, user 101 has selected a first microplate having the identifier "Plate 1" as shown in pane 290. Microplate identifier window 280 represents this microplate by a highlighted rectangle in window 280. Other microplates selected by user 101 may also be represented in this window, such as Plate 2 represented by an un-highlighted rectangle in window 208, and user 101 may highlight any one of them to select it and thus cause its identifier to be displayed in pane 290.

A layout window 220 is included so that user 101 may indicate where probe material obtained from the wells of the highlighted microplate (i.e., "Plate 1" in this example) are to be placed as probes. Window 220 shows a simulated substrate 222, which may for example represent a glass slide. A portion of the glass slide, shown as portion 222A, may be frosted in some implementations and thus not used for depositing probes. Four portions of probe arrays, represented by probe array portions 230A-D (generally and collectively referred to as portions 230), are shown in window 220. Probes in each of portions 230 in this example were deposited based on probe material obtained from Plate 1. If user 101 had highlighted Plate 2 in window 280 in this example, then different array portions would have been shown in window 220 corresponding to the location of probes derived from depositing of probe material from the microplate represented by Plate 2. For example, probes derived from Plate 2 may be located in probe portions that would be represented by four rectangles, each of which would be adjacent in the same sense to one of portions 230 (see FIG. 2C described below). More generally, by specifying the location of probe array portions derived from different microplates (or from the same microplate in subsequent spotting operations), user 101 may cause probe material from a well of one microplate to be deposited on top of probes from another well of another, or the same, microplate. Thus, one or more targets (or compounds resulting from a combination of targets due to co-location of spotting) may be added selectively to one or more probes (or compounds resulting from a combination of probes due to co-location of spotting).

There are four portions 230A-D in this example because it is illustratively assumed that the printing head of this example (described below) has four pins that each simultaneously deposit a probe at each of the portions. The spacing apart of the four pins with respect to each other thus corresponds to the spacing apart of the four probe array portions 230. The location of portions 230 on substrate 222 may be selected by user 101 by providing x and y coordinates in panes 240. These coordinates may specify, for example, a relationship between a top-leftmost probe in the top left portion (portion 230A) in relation to the top left corner of substrate 222, although numerous other techniques for specifying location on the substrate may be used. Also, using replicate positions window 250 in accordance with this illustrative example, user 101 may specify that probes may be replicated at various locations. Thus, for example, user 101 may specify that probes in portions 230 are to be replicated at locations below those shown for portions 230 in FIG. 2, on top of portions 230, or at any other location on substrate 222. User 101 may specify using replicate number pane 257 that any number of replicates may thus be produced. These replicates may be deposited on separate substrates (e.g., two or more microscope slides) in some implementations, as indicated by a number entered by user 101 into slide number pane 255.

Using zoom buttons 223, user 101 may magnify any of portions 230 to show the specific location of probes that will be spotted from wells of Plate 1 onto one or more probe arrays on the substrate represented by simulated substrate 222. The zoom feature typically may be used in conjunction with pages 240 and/or 250 to provide highly selective placement of probes. The only constraint in this implementation on the placement of probes is that, if a number n of multiple pins are used, then the spacing of those n probes in relation to each other is determined by the spacing of the pins. However, a single pin may be used in some implementations. Thus, user 101 is provided with complete flexibility with respect to the location of individual probes on substrate 222 (or on multiple substrates), including multiple deposits on a same spot.

Figure 2C:
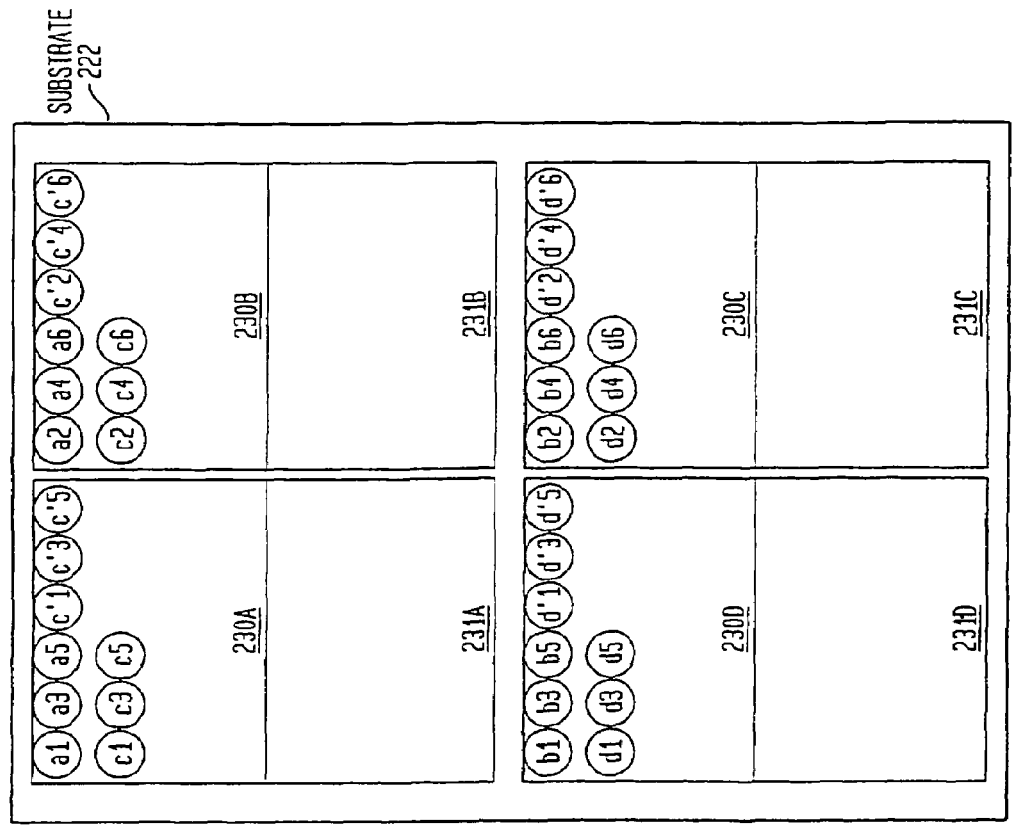
FIGS. 2B-2D are schematic representations of illustrative techniques for using printing pins to deposit probes in accordance with placements specified by a user employing the interface of FIG. 2A.
Figure 2B:
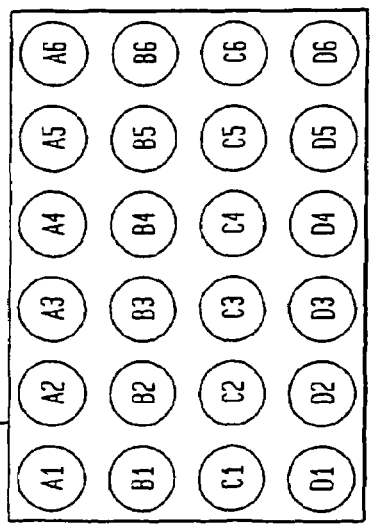
Figure 2D:
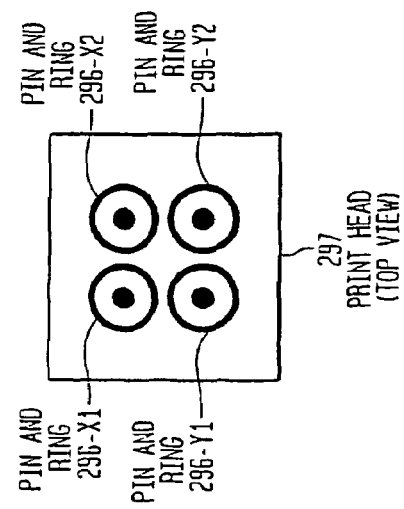

FIGS. 2B and 2C show in greater detail illustrative layouts of probes within probe portions 230 in relation to the wells from which the probes were obtained. FIGS. 2B and 2C are not drawn to scale; the probe spots shown in FIG. 2C are much larger in relation to the wells of FIG. 2B, for example, than typically would be the case. It is illustratively assumed that FIG. 2C is a magnified representation of a portion of substrate 222 including probe portions 230 of FIG. 2A as well as adjacent probe portions 231A-D. Portions 231 may be illustratively assumed to have been deposited using probes from Plate 2 as represented by rectangle 2 of window 280. It is also illustratively assumed that the print head has four printing pins spaced apart so that they (and their ring assemblies, described below) align with centers of any four mutually adjacent wells of plates 1 or 2. For example, it is assumed for convenience of illustration that the printing pins and associated rings are arranged in two rows (X and Y) and two columns (1 and 2) so that when pin and ring X1 (the elements of which may also be referred to for simplicity as pin X1 or ring X1) is aligned with the center of well A1, pin and ring X2 is aligned with well A2, pin and ring Y1 is aligned with well B1, and pin and ring Y2 is aligned with well B2. FIG. 2D is a simplified top-view schematic representation of four pin and ring assembles of an illustrative print head 297 arranged in the described configuration.

In a first spotting operation, the rings of print head 297 are dipped into wells A1, A2, B1, and B2 to pick up probe material from those wells of Plate 1. In a manner to be described below, print head 297 is moved to a location above the substrate as specified by user 101 with respect to substrate 222 and the pins lowered toward the substrate. Probe spot a1 thus is formed by pin X1 using the probe material in well A1. Probe spot a2 (which is the same distance from probe spot a1 as well A2 is from well A1 and pin X2 is from pin X1) thus is formed by pin X2 using the probe material in well A2. Similarly, probe spot b1 is formed by pin Y1 using the probe material in well b1, and probe spot b2 is formed by pin Y2 using the probe material in well B2. Probe spots a1 and b1 are thus separated by the same distance that separates the centers of wells A1 and B1 and that separates pins X1 and Y1, although it does not appear so because FIG. 2C is not drawn to scale so that the described features may be more clearly seen.

User 101 may indicate in replicate number pane 257 that any number of replicates of probe spots a1, a2, b1, and b2 are to be deposited on substrate 222. For example, user 101 may specify 2 replicates by this technique or any other of various known techniques and replicate spots will be deposited using additional probe material stored locally to each pin in its associated ring, as described below. Also, user 101 may specify in slide number pane 255 that replicates be deposited on any number of slides (or other substrate). For example, user 101 may specify "48" in pane 255 so that, after depositing spots a1, a2, b1, and b2 on one slide, the print head is moved to another slide where the same probes are deposited in the same relative positions on that next slide, and so on until the pattern and probe material content of probes a1, a2, b1, and b2 have been repeated on 48 slides. If user 101 specifies both that 48 slides and 2 replicates should be printed, then 96 patterns such as that of probe spots a1, a2, b1, and b2 will be printed. Typically, these replications and multiple slide printings occur without the need to return to Plate 1 for additional probe material because the rings hold sufficient material for numerous printings, as described below.

After completing the printing of probe spots using probes from wells A1, A2, B1, and B2, print head 297 of the illustrated implementation moves to wash and dry stations where remnants of those probe materials are removed, as described below. As also described below, print head 297 then may return to the well plate area to obtain probe materials from the same (e.g., if a large number of replicates are being printed such that sufficient material is not held in the rings) or a different group of four wells. This next group of wells may be from Plate 1 or it may be from another microplate. It is illustratively assumed that the next group is from Plate 1 and that print head 297 moves incrementally by two wells across horizontal rows of Plate 1 as shown in FIG. 2B. Thus, probe materials from wells A3, A4, B3, and B4 are picked up and then deposited to form probe spots a3, a4, b3, and b4 as shown in FIG. 2C. In other implementations, any other number of wells may be incremented in each spotting operation or, as noted, wells may be repeated. Start and end well panes 280 and 285 enable user 101 to specify wells at which spotting operations should start and end.

It is now assumed that incremental steps of two columns are repeated across the first two rows of Plate 1 such that probe materials from all of the wells in the first two rows are deposited in accordance with the replication and slide numbers specified by user 101, as indicated by the placement of probe spots a1-a6 and b1-b6 in FIG. 2C. In the illustrated implementation, the incremental steps are then repeated across the third and fourth rows, C and D of Plate 1, respectively. If user 101 selects the "Array" button in pattern pane 270, print head 297 will place probe spots from wells in rows C and D under those previously placed so as to build up an array, as indicated by the placement of probe spots c1 through c6 and d1 through d6 of FIG. 2C. To implement one of many possible alternative configurations, user 101 may select the "Linear" button of pane 270 so that the probe spots are placed across the same row as those derived from wells in rows A and B, as represented by probe spots c'1 through c'6 and d'1 through d'6 of FIG. 2C.

User 101 may specify that another microplate, for example Plate 2, be used for additional spotting operations. As noted, user 101 may specify that the probes from the Plate 2 operation be placed as indicated by probe portions 231 shown in FIG. 2C. Alternatively, as noted, the probes derived from Plate 2 may be deposited on top of those derived from Plate 1 if user 101 specifies the location of probe portions 231 to be the same as the location of probe portions 230. Also, dot-spacing panes 245 enable user 101 to specify the spacing between probes in the x and y directions. For example, as indicated in this illustration, user 101 has specified that individual probes spots are to be spaced at distance of 375 microns center to center in both the x and y directions. Other distances in either or both directions could be specified. As will now be appreciated by those of ordinary skill in the relevant art, numerous combinations and variations of the aforementioned probe placement techniques may be employed so that user 101 has wide flexibility in selecting probe patterns using GUI 200, or using other interfaces or techniques in other implementations.

Figure 3:
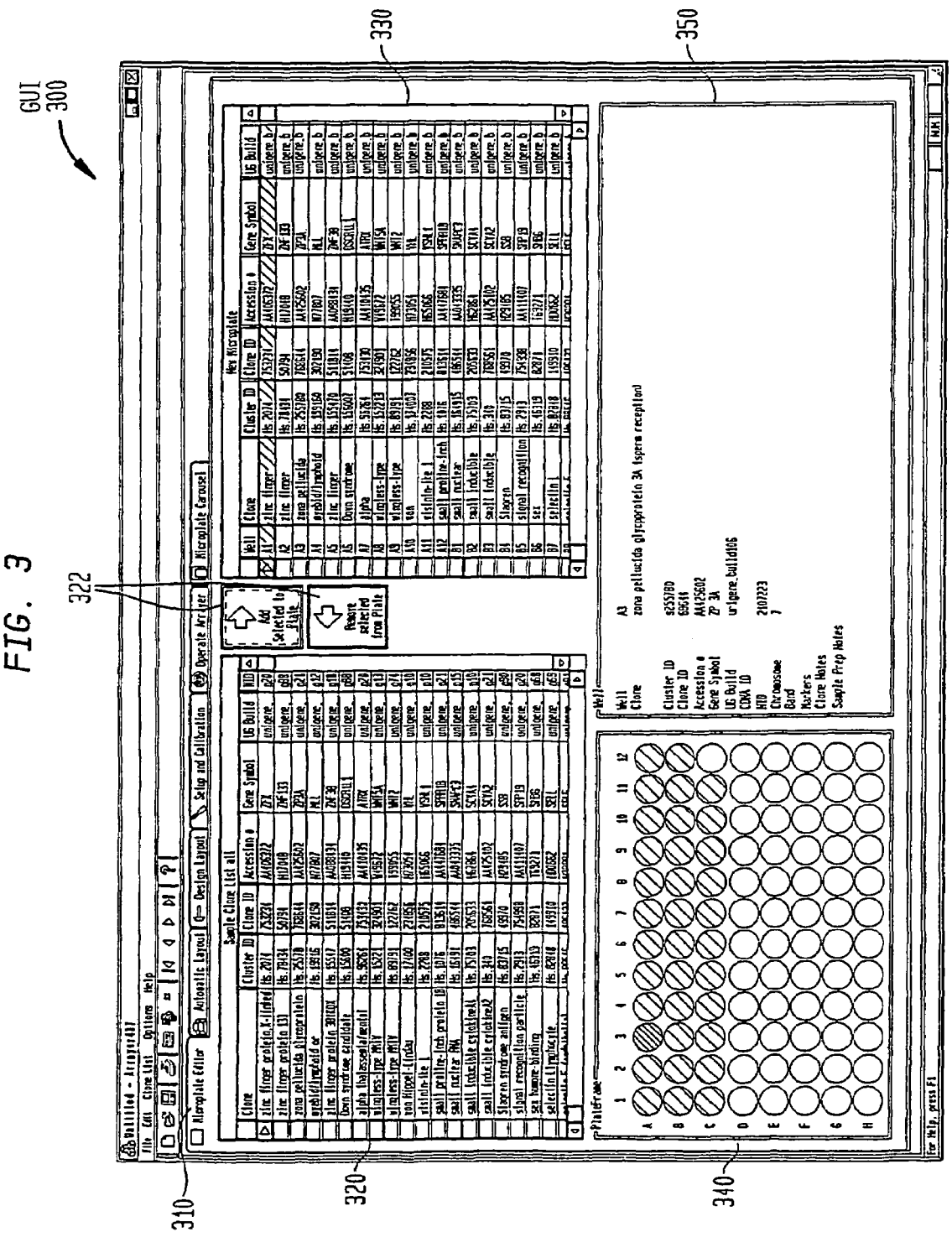
FIGS. 3 through 6 are additional illustrative embodiments of graphical user interfaces generated and maintained by the computer of FIG. 1 to enable a user to control the operation of the arrayer of FIG. 1.

FIG. 3 illustrates additional operations that may be performed by user 101 employing microplate editor tab 310 of GUI 300. GUI 300 includes four windows in this illustrative implementation: source probe list window 320, microplate probe list window 330, microplate well display window 340 and microplate well list window 350. Source probe list window 320 displays available probe materials (e.g., "zinc finger protein 133" clones in this example) that may be included in wells of a microplate and thus available for spotting into probe arrays. The probe data upon which this list is constructed may be input and/or updated by user 101 in any of various conventional ways and/or downloaded from various sources including probe material suppliers' lists. The probe data is stored in this implementation in system memory 170. Using selection buttons 322, or in any of numerous other conventional ways, user 101 selects probes from window 320 and adds or removes them from microplate probe list window 330. Microplate well display window 340 shows an illustrative configuration of wells in a conventional 96-well plate (similar to the illustration of FIG. 2B). As indicated, any other configuration and/or number of wells may be employed in other implementations. The contents of a well selected by user 101 from window 340, and genomic or other information related to those contents, are listed in window 350. Thus, windows 320, 330, 340, and 350 interact in response to selections by user 101. For example, user 101 may select a probe from the list in window 320 and select it for placement in a well (such as highlighted well A1 of the illustrated example) as indicated in window 330. After assigning probes to various wells of the microplate in this manner, user 101 may click on, or otherwise select, a representation of a well in window 340 and see in window 350 the genomic and other information related to the probe in the selected well.

Figure 4:
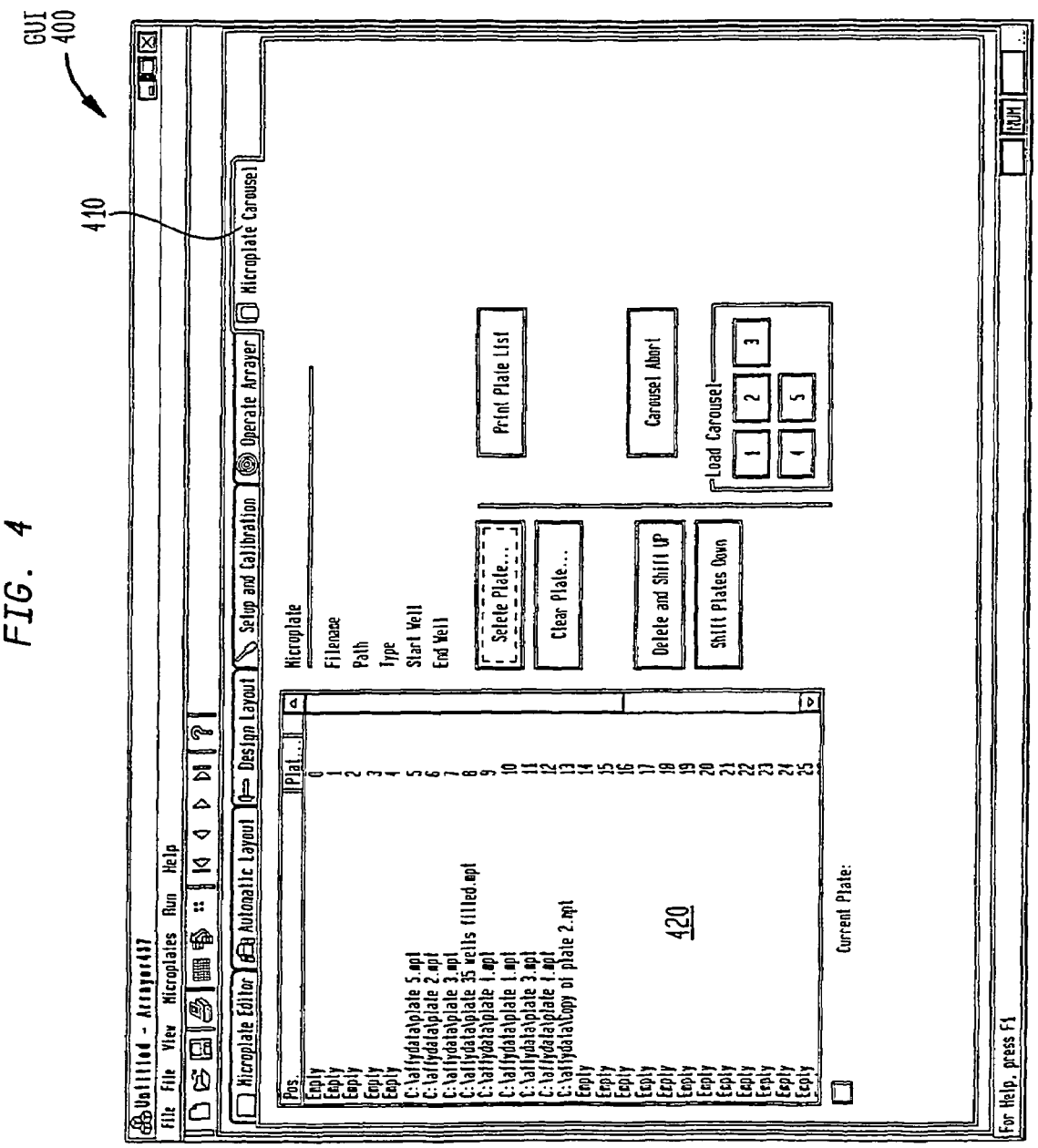

FIG. 4 illustrates additional operations that may be performed by user 101 employing microplate carousel tab 410 of GUI 400. Microplate list window 420 displays a list of microplates with their microplate identifiers as discussed above with respect to pane 290 of FIG. 2A. In one of many possible implementations, user 101 may click on an empty space in window 280 to call up a dialog box for naming a microplate, which is then represented in window 280 as described above with respects to Plates 1 and 2. User 101 may select and move any of the microplate identifiers shown, for example, in the left column of window 420 of FIG. 4 so that it aligns with any carousel slot number. This alignment designates that user 101 intends that the selected microplate will be loaded in the corresponding carousel slot. Using a bar code reader or other technique, spotting system 199 may optionally ensure that user 101 has correctly loaded the identified microplate into the corresponding carousel slot prior to depositing probes from the microplate onto slides. For example, in some implementations, user 101 may employ a bar code reader (e.g., one of input/output devices 171) to scan a bar code on a surface of a microplate, or manually enter a bar code using a keyboard of devices 171, so that the microplate is uniquely identified to executables 172. Executables 172 correlates user-selected carousel slots with microplate identifiers so that, if user 101 has correctly placed a microplate in the selected slot, the identify of the microplate associated with each selected carousel slot are stored in an appropriate data storage structure such as user-entered experiment data 178 in system memory 170. Further aspects of the reading of bar codes are described below in relation to the operations of microplate robot 730, and in U.S. patent application Ser. No. 09/907,196, filed Jul. 17, 2001, which is hereby incorporated herein by reference in its entirety. Other information related to the operation or experimental setup of arrayer 100 may also be stored in experiment data 178. For example, information may be stored regarding user selections made using GUI's 157 (as described, in non-limiting examples, in relation to FIGS. 2A-D and 3-6), setup of microplates in carousel 720, types of microplates used, setup of slides on platen 740, temperature and/or humidity settings in control chambers, reagents used in washing or drying, and other variables of spotting operations described below.

Figure 5:
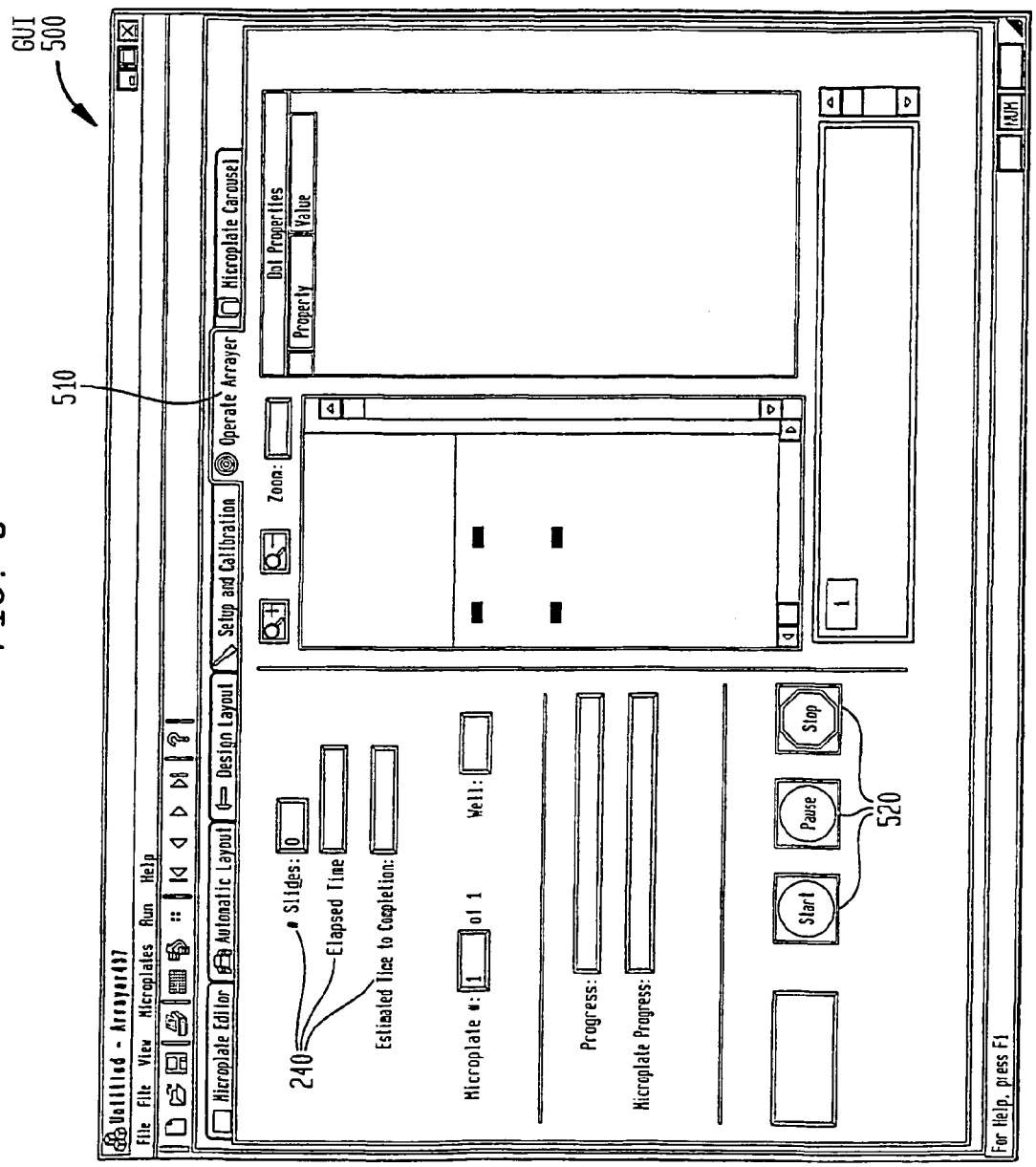
Figure 6:
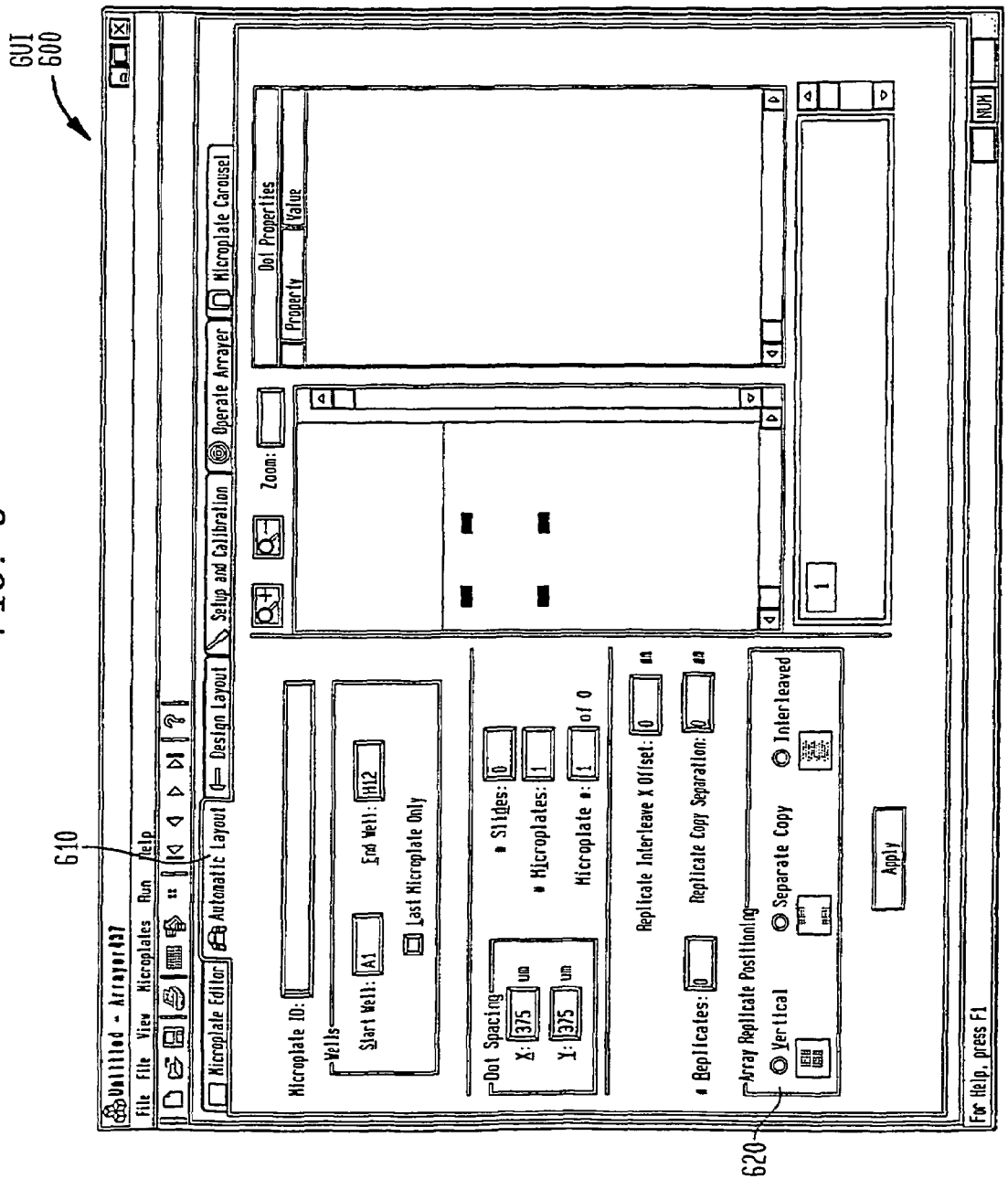

FIG. 5 illustrates additional operations that may be performed by user 101 upon selecting operate arrayer tab 450 of GUI 500. As indicated by buttons 520, user 101 may cause arrayer 100 to start, stop, or pause in its operations (e.g., printing, washing, obtaining cloning material from microplates, retrieving or returning microplates from or to the carousel, and so on as described below). Those of ordinary skill in the relevant art will appreciate how such operations may be executed by executables 172 in cooperation with other elements of computer 150 and arrayer 100 as described below. Information panes 240 provide user 101 with information regarding the number of slides being printed, elapsed time of the printing operation, and estimated time to completion. FIG. 6 is a graphical representation of an illustrative GUI 600 activated by user selection of automatic layout tab 610. User 101 may select one of automatic positioning tabs 620 so that pre-programmed patterns of probes in any number of probe arrays on any number of substrates are implemented. Thus, the functions shown and performed in accordance with GUI 600 are similar to those described above with respect to GUI 200 except that user 101 generally has less flexibility in designing specific patterns of probes if GUI 600 is selected than if GUI 200 is selected. An advantage is ease of use in allowing user 101 to specify pre-programmed patterns such as interleaving of probes, vertical orientation of probe arrays, and so on.

Figure 7:
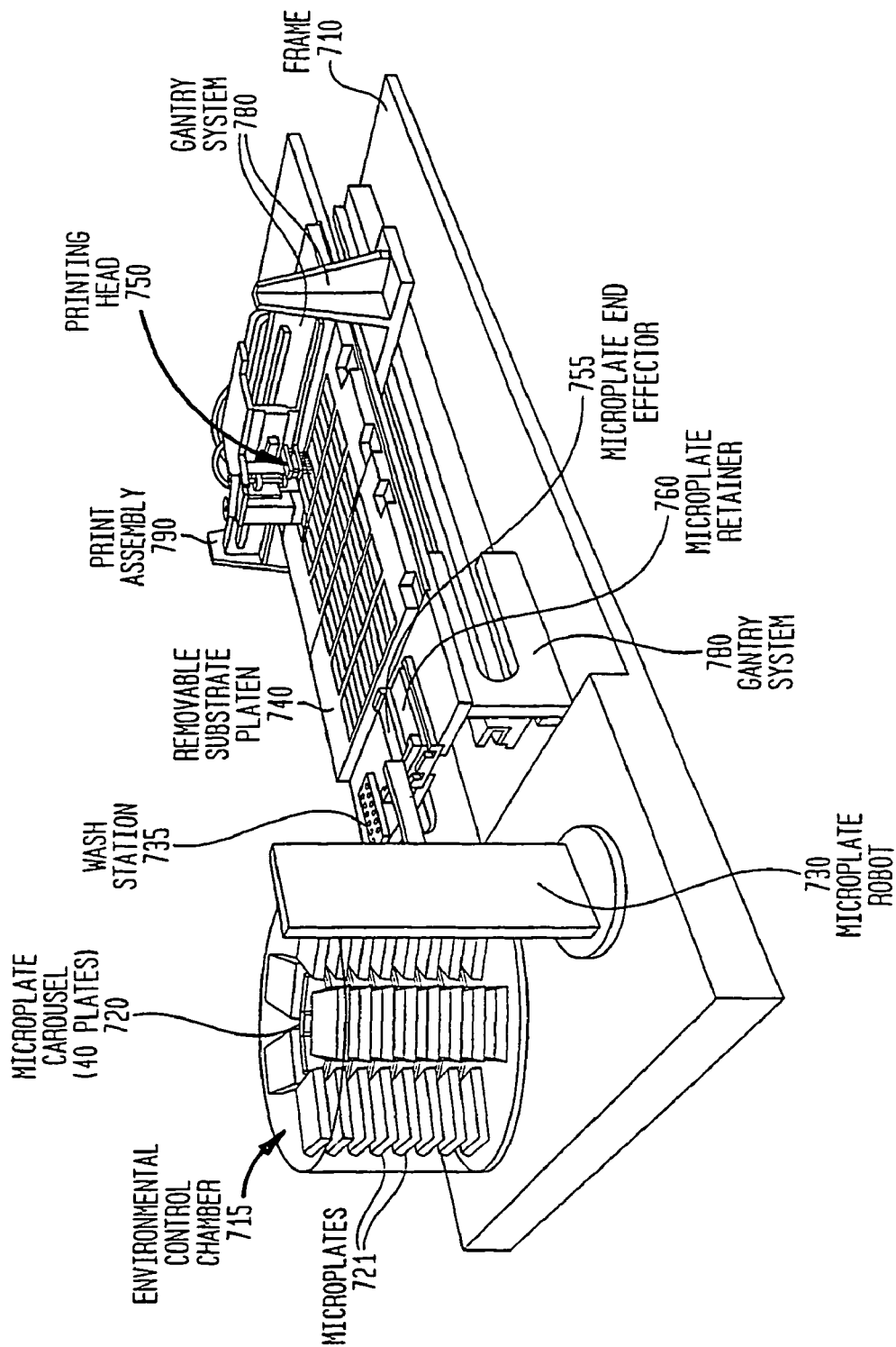
FIG. 7 is a simplified schematic perspective drawing of one embodiment of an arrayer of the system of FIG. 1.

Arrayer 100: FIG. 7 is a simplified schematic perspective drawing of one preferred and non-limiting embodiment of arrayer 100 showing an illustrative arrangement of some of its functional elements. Arrayer 100 includes in this illustrative arrangement microplate carousel 720 situated within environmental control chamber 715. In some implementations, one or more environmental control chambers may also be provided to cover platen 740, gantry system 780, wash station 735, and/or other areas in which probe material may be present at any point in the spotting operation. In a preferred embodiment, these additional control chambers may be controlled independently of control chamber 715. Thus, as a non-limiting example, control chamber 715 may be maintained at a temperature and/or humidity suitable for relatively longer term storage and to prevent evaporation or degradation of probe material, while the other one or more control chambers are maintained at a temperature and/or humidity suitable for shorter term spotting operations. Sensors and actuators of carousel 720, described below, are also represented schematically as aspects of sensors 106 and motors/actuators 108 of FIG. 1. Carousel 720 and chamber 715 are structurally connected to other elements of arrayer 100 by frame 710. A microplate robot 730 selectively moves, employing aspects of sensors 106 and motors/actuators 108 under control of executables 172, a microplate stored in slots of carousel 720 to a microplate retainer 760. When a microplate is in retainer 760, it is registered so that ring mechanisms of the illustrated pin and ring print head assembly may correctly access wells of the microplate as specified by user 101 employing, for example, GUI's 300 and 400 described above. An illustrative print head assembly 750 is shown in an implementation in which 12 pins and rings are provided rather than the configuration of four pins and rings described above. Microplate end effector 755 assists in the reliable transfer of selected microplates from carousel 720 to retainer 760. Substrates, which are illustratively assumed to be microscope slides in this example, are positioned on a removable substrate platen 740 in this implementation. Thus, slides may be removed together with platen 740 after a printing operation has been completed. The removed platen and slides may thus conveniently be subjected to further processing or put in temporary storage prior to further processing, while another platen with slides is inserted for printing by arrayer 100. These, and other, components of arrayer 100 are now described in greater detail with respect to illustrative and non-limiting implementations.

Figure 8C:
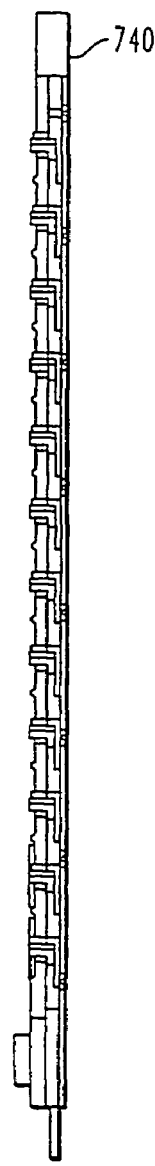
Figure 8D:
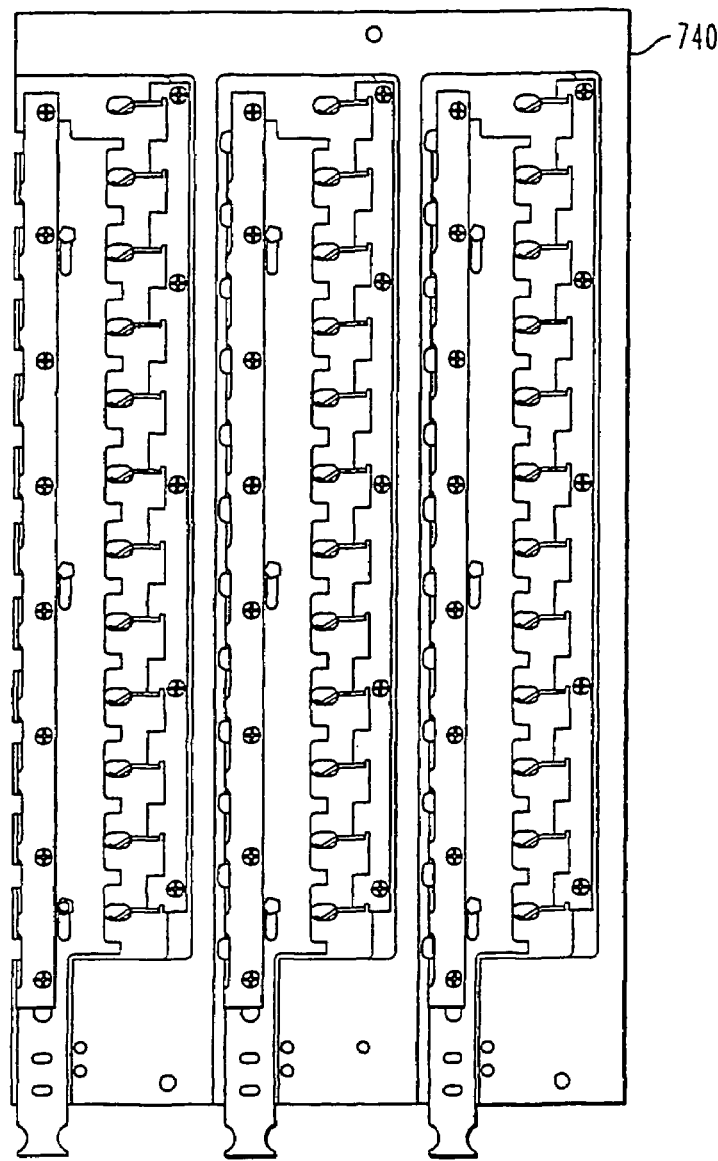
Figure 8E:
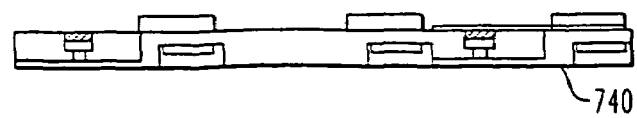

FIGS. 8A-8E are schematic representations in related views of one embodiment of platen 740 including holding assemblies for securing and registering multiple slides to the platen. (FIGS. 8A and 8C are lateral side views, FIG. 8E is an end side view, FIG. 8B is a top view, and FIG. 8D is a bottom view.) FIG. 9 is a simplified schematic representation of detail 899 of FIG. 8. In the following description of platen 740 and of its features for holding microscope slides, the slides typically may be assumed to be standard glass microscope slides having flat surfaces without indentations or wells on the surface of the slides. However, various types of slides may be used. In the illustrated implementations, the microscope slides are held on the flat upper surface of platen 740. FIG. 8B is a top view of platen 740 showing mechanisms for holding the slides securely in place in a manner that allows rapid registration of slides in parallel. Platen 740 registers the slides relative to printing head 750 that is lowered and raised to effect the spotting of a sample onto the microscope slide. Platen 750 in the illustrated example can accommodate 108 standard microscope slides in rows and columns. As shown in detail 899 of FIG. 9, platen 740 includes reference tabs 910 that contact and reference each slide, as well as a spring-loaded mechanism with clamps 920 for contacting two edges of each slide to secure and align multiple slides in two dimensions in a parallel operation. In these implementations as represented in detail 899, the remaining two edges of the slides need not be contacted with any retaining mechanism as the clamps are sufficient to secure the slides to the surface of the platen. Parallel engagement mechanisms 930 may be pulled in engage-travel direction 930 to cause spring clamps 920 to engage multiple slides in parallel. In particular, this movement enables spring-loaded mechanisms 920 to push the microscope slides against opposing reference tabs 910 and thus secure the slide. Mechanisms 930 may be pushed in opposing disengage-travel direction 932 to disengage the multiple slides in parallel. While platen 740 is removable from frame 710 of the illustrated implementation, it generally is not moveable in the sense that the platen and slides do not move relative to the printing head during the spotting operation.

Printing head 750 in this illustrative embodiment includes a single activator for a single axis that forces the downward motion of the printing head to be coaxial as it deposits a probe onto a microscope slide. In a preferred implementation, the printing head can accommodate 1, 4, 8, 12, 32 or 48 pairs of pin and ring elements to deposit spots of fluid probes onto the glass slides. (For convenience, either a pin or a ring, or both, may sometimes referred to herein as a "depositing element.") Aspects of a pin and ring assembly in particular implementations, as well as a depositing device and its operation, are described in U.S. Pat. No. 6,269,846, which is hereby incorporated by reference herein in its entirety for all purposes. Generally, the ring of the pin and ring mechanism in one implementation includes a circular ring section formed from a circular piece of metal. The width or outer diameter of the ring is greater than its length. The ring is attached at the end of an arm section that extends from a cylinder. The ring has a uniform surface area and, in some implementations, includes no open-sided section or any indentation into its wall. That is, the top and bottom edges of the ring are uniform, except at the point of attachment of the top edge to the arm. The ring and the cylinder section are interconnected by the arm so that the opening in the ring aligns with the opening in the cylinder. The arm typically is unitary with both the cylinder and the ring. However, the arm may be any structure of sufficient integrity to interconnect the cylinder and the ring.

The pin in one preferred implementation is a single, rod-like device having at one end a very narrow tip. The pin is not hollow, but instead, in a preferred implementation, is fashioned from a solid piece of metal. During operation, the pin is inserted into and through the cylinder with the tip being capable of moving freely through the opening of the ring. The pin and ring mechanism, in some implementations, may measure approximately 1.5 inches when the cylinder and ring are inserted over the pin. The very bottom of the tip of the pin typically is flat, and is uniformly perpendicular to the sides of the pin, forming a ninety degree angle to the sides. This feature assists, in some implementations, in delivering a fluid sample to a substrate as discussed below.

Figure 10A:
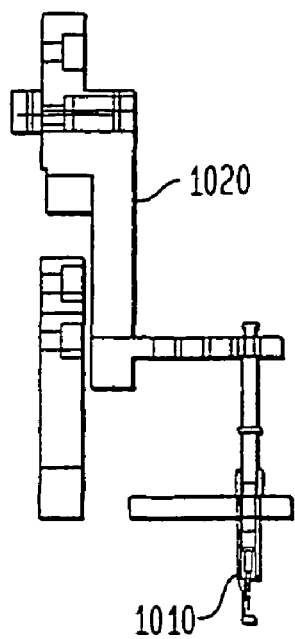
FIGS. 10A and 10B are simplified schematic representations in related views of illustrative embodiments of pin and ring spotting assemblies such as may be used in the spotting mechanisms of the arrayer of FIG. 1, FIGS. 10C and 10D are simplified schematic representations in related views of illustrative ring assemblies.
Figure 10B:
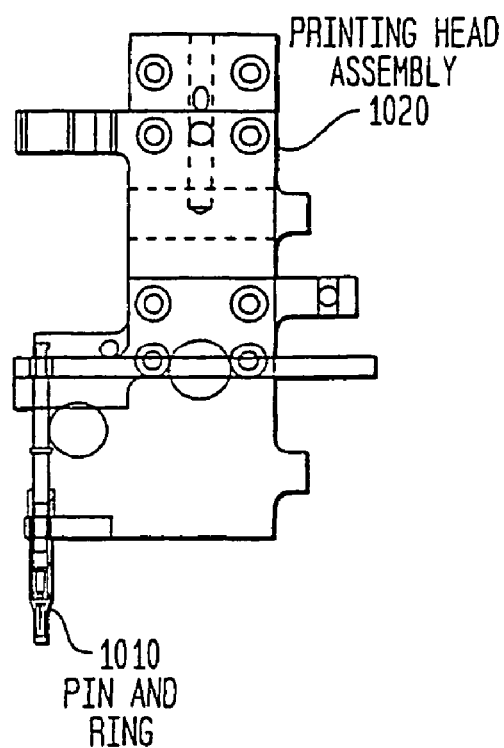
Figure 10C:
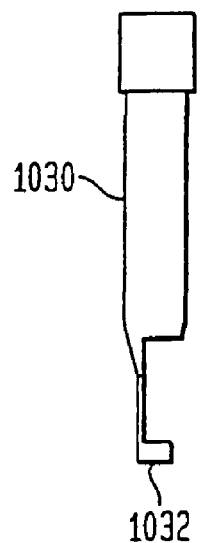
FIG. 10E is a simplified schematic representation of an illustrative pin assembly.
FIGS. 10F and 10G are simplified schematic representations in related views of illustrative pin assemblies within the ring assemblies in seated and unseated positions, respectively.
Figure 10D:
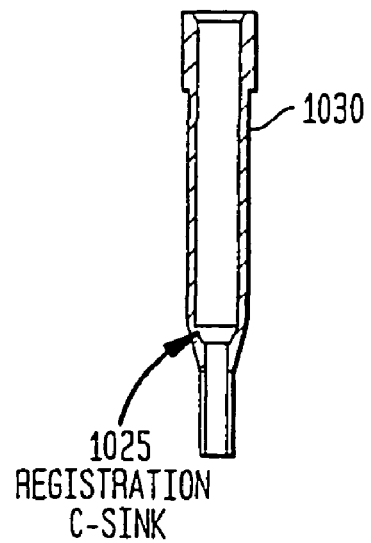
Figure 10E:
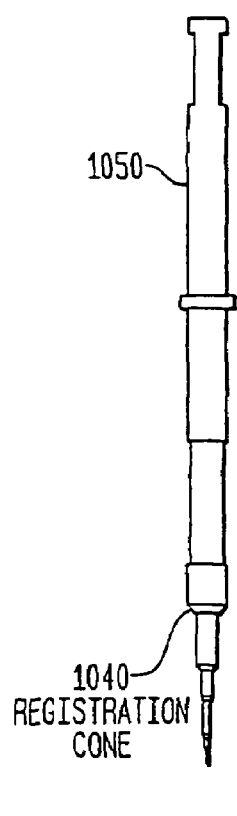
Figure 10F:
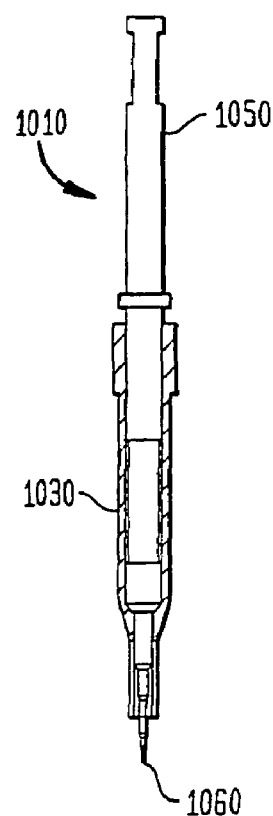
Figure 10G:
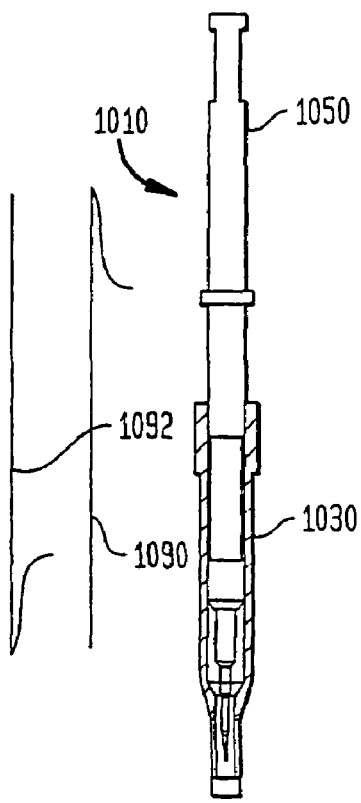

In some implementations, the pin and ring include male and female countersink portions for proper alignment of the pin through the ring opening during the spotting process. The countersink and other features of illustrative pin and ring implementations are shown in FIGS. 10A-10G. In particular, FIGS. 10A and 10B are simplified schematic representations in related views of illustrative printing head assembly 1020 including pin and ring assembly 1010. FIGS. 10C and 10D are simplified schematic representations in related views of illustrative ring assembly 1030. FIG. 10C includes a side view of ring portion 1032 in which probe material is retained. This material thus serves as a local reservoir of probe material that is transferred to the tip of the pin as it passes through the meniscus formed in ring portion 1032. FIG. 10E is a simplified schematic representation of an illustrative pin assembly. Shown in FIG. 10E is illustrative pin assembly 1050 including registration cone portion 1040 that is capable of seating with a registration sink portion 1025 of ring assembly 1030. FIGS. 10F and 10G are simplified schematic representations in related views of pin and ring assembly 1010. In FIG. 10F, pin assembly 1050 is descended (indicated by direction 1092) within ring assembly 1030 so that registration elements 1025 and 1040 are engaged. In this configuration, tip 1060 of pin assembly 1050 is exposed for depositing probe on the microscope slide. In FIG. 10G, pin assembly 1050 is retracted up (indicated by direction 1090) within ring assembly 1030 so that tip 1060 is above ring portion 1032 and is ready to descend through the meniscus for subsequent depositing of probe.

FIGS. 11-14 are more detailed perspective views of various aspects of an illustrative implementation of microplate robot 730 of the preferred implementation shown schematically in FIG. 7. As noted with respect to FIG. 7, robot 730 determines (under the control of computer 150 and executables 172) that user 101 has loaded a carousel slot with the intended microplate, selectively retrieves one of microplates 721 from the slot through an opening in environmental control chamber 715, transfers the selected microplate to microplate retainer 760, and removes a top lid from the microplate so that the ring assemblies of printing head 750 may descend into the wells to obtain probe material. In the illustrative implementation shown in FIG. 7, carousel 720 is divided into five segments of slots, each segment extending radially from a central vertical axis, with each segment capable of providing slots for eight microplates. In some implementations, the microplates may be stacked upon each other rather than placed in slots. It will be understood that the particular configuration of carousel 720 shown in FIG. 7 is illustrative only, and that numerous designs may be employed in other implementations. Moreover, the word "carousel" is used for convenience only, and should be read broadly to include various designs for microplate holders, whether or not circular and whether or not revolving around a vertical axis. Carousel 720 is environmentally controlled by use of chamber 715 under the control of executables 172 in this implementation in order, among other things, to limit evaporation of probe materials in the microplates. An access door (not shown) allows user 101 to insert the microplates into carousel 720 at desired locations. In the illustrated implementation, the microplates are supported within carousel 720 by tabs extending from the sides of the segments.

Figure 11:
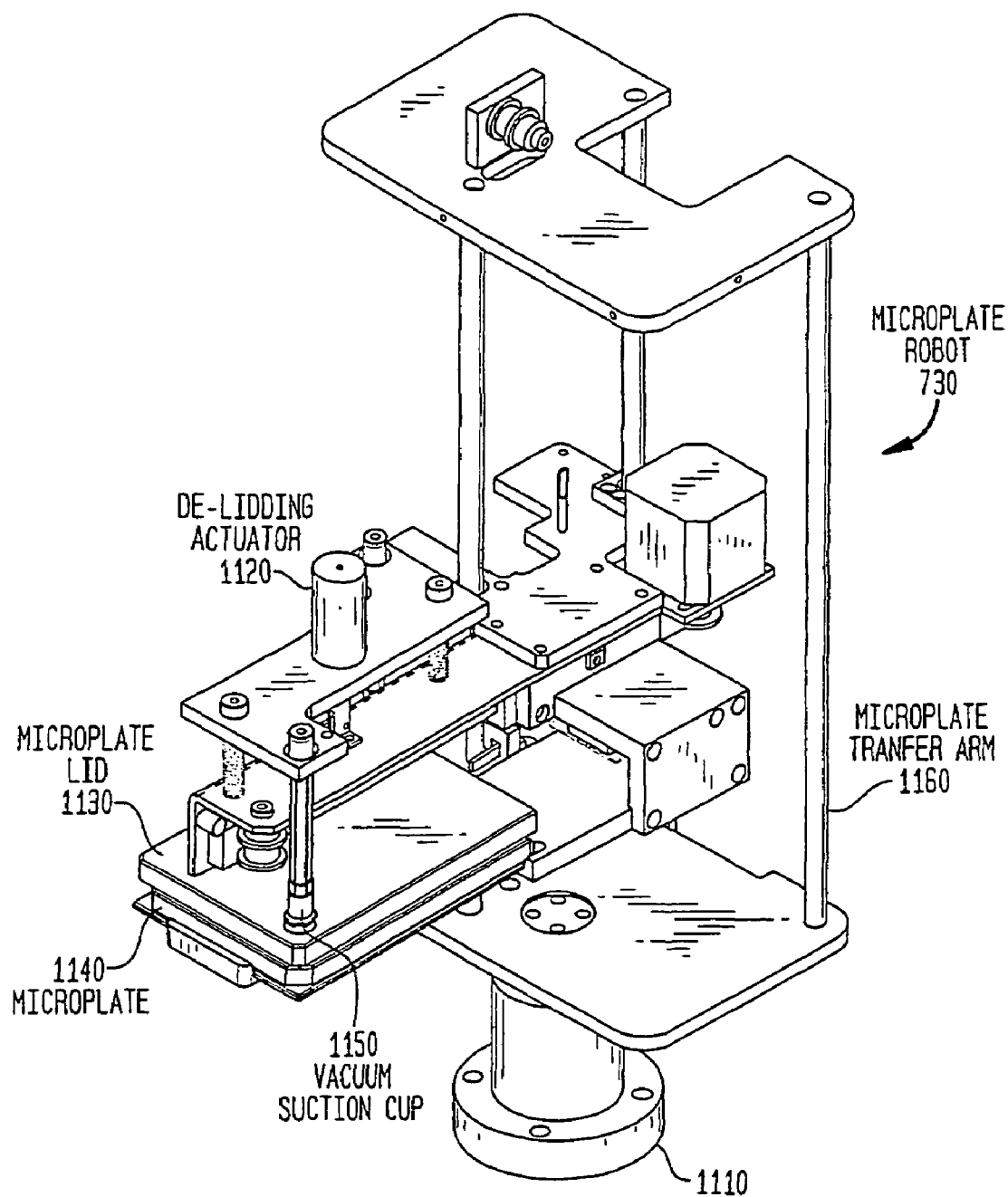
FIG. 11 is a perspective view of one embodiment of a microplate robot of the arrayer of FIG. 7, including mechanisms for holding the microplate, removing its lid, and identifying the microplate by barcode scanning.

To provide further detail, FIG. 11 is a perspective view of an illustrative embodiment of robot 730 showing mechanisms for holding the microplate, removing its lid, and identifying the microplate by reading a one- or two-dimensional bar code or employing any of various other machine-readable indicators (e.g., signal transmitter or transducer, or other device, any one or more of which are referred to for convenience herein simply with reference to "barcode") known to those of ordinary skill in the relevant art. In this implementation, robot 730 also returns a microplate to carousel 720 after it has been used to supply probe material, although microplates that have been processed may be stored elsewhere (such as adjacent to microplate retainer 760) in other implementations.

Figure 12:
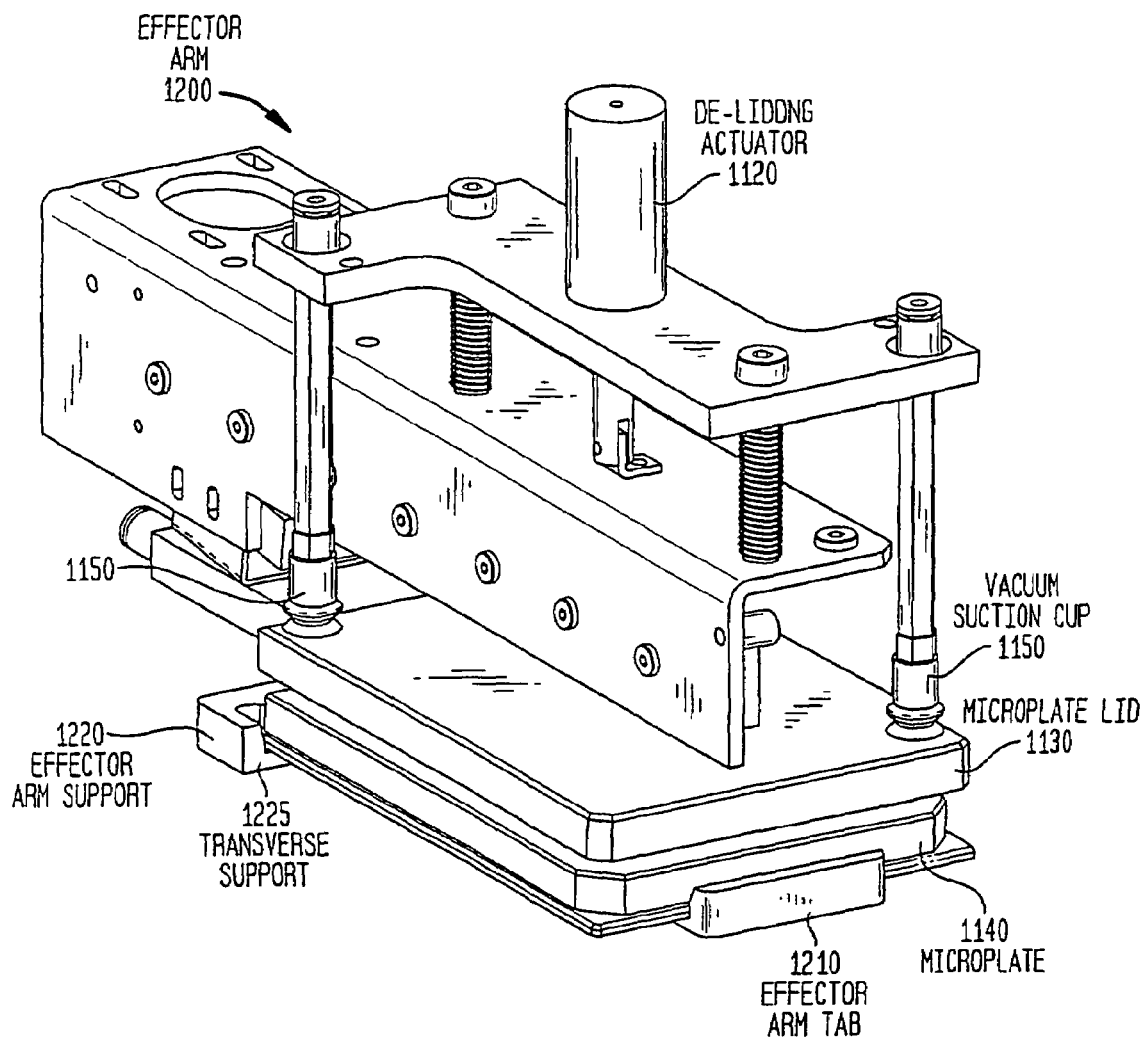
FIG. 12 is a perspective view of aspects of the microplate robot of FIG. 11 including mechanisms for holding the microplate and removing its lid.
Figure 13:
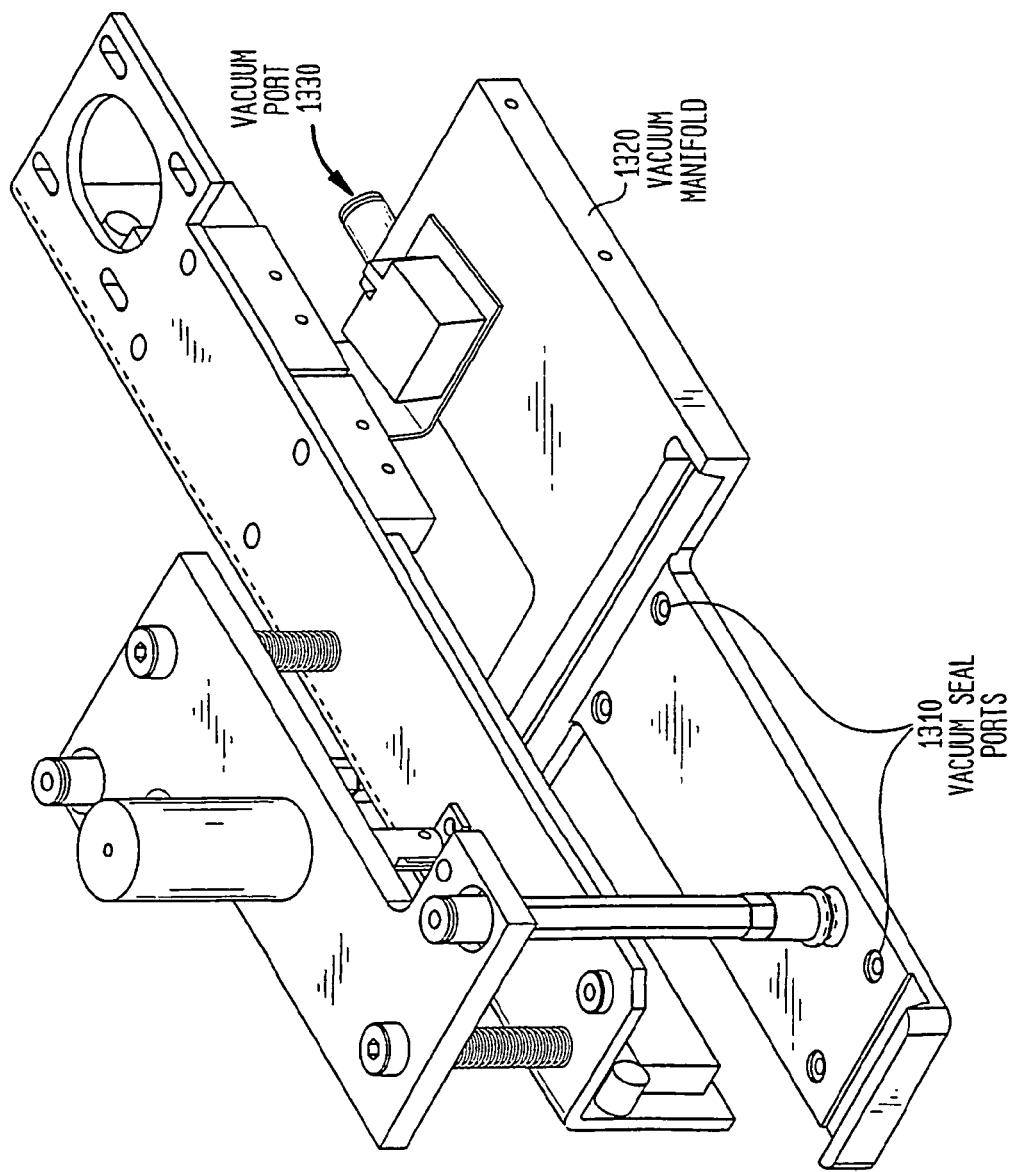
FIG. 13 is a further perspective view of aspects of the microplate robot of FIGS. 11 and 12.
Figure 14:
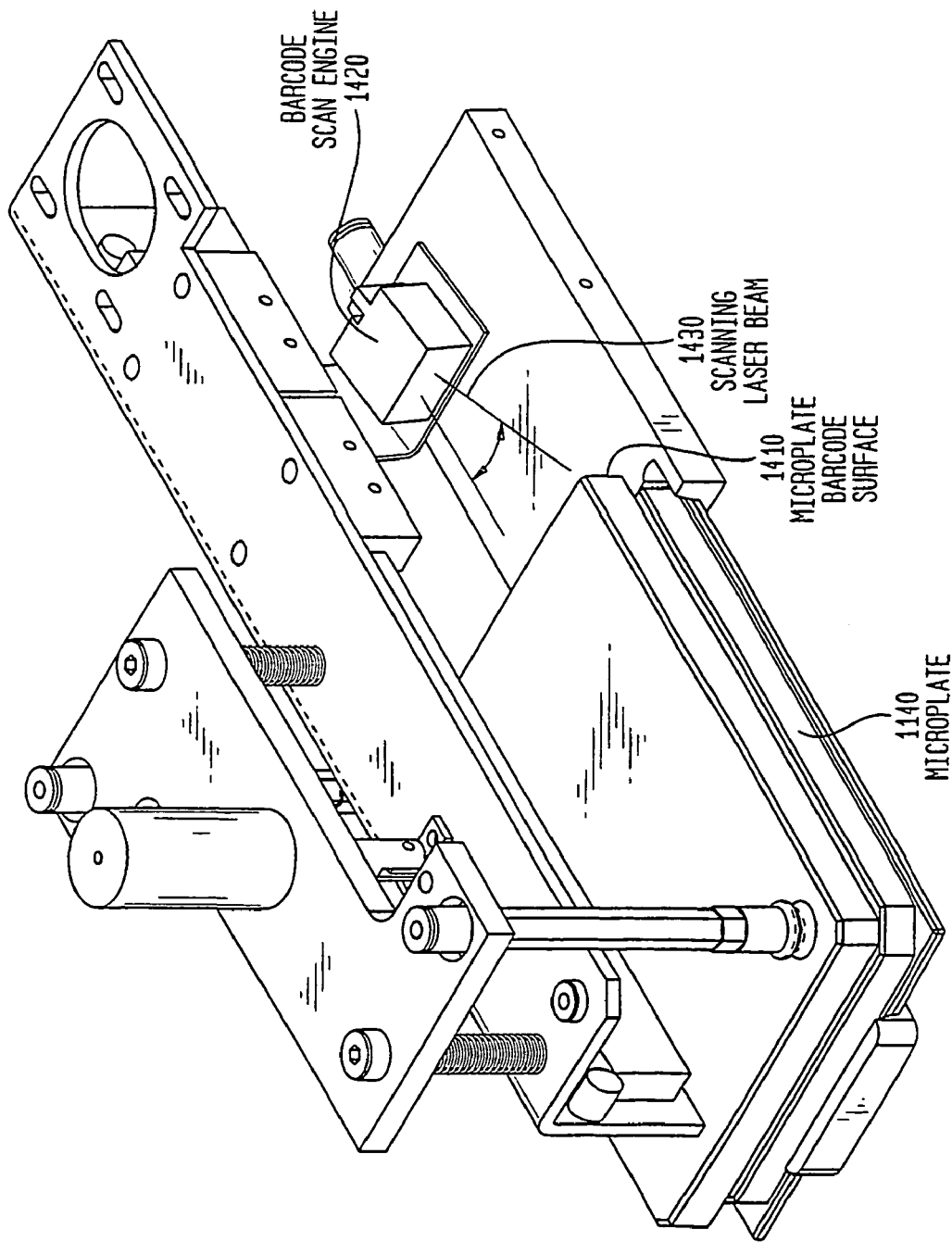
FIG. 14 is a further perspective view of aspects of the microplate robot of FIGS. 11-13, including mechanisms for scanning bar codes on the edge of a microplate.

As shown more clearly in FIG. 12, robot 730 includes effector arm 1200 that supports the microplate from underneath during removal and return of the microplate. Effector arm 1200 is moved in manners described below by aspects of motors and actuators 108 shown schematically in FIG. 1. Effector arm 1200 in this implementation includes a longitudinal support section 1220 that terminates with an upwardly extending tab 1210. The length of longitudinal support 1220 is sufficient to allow the microplate to rest on the support with tab 1210 extending beyond the end of the microplate. Tab 1210 prevents the microplate from sliding off of the end of the support during transfer of the microplate from carousel 720 to microplate retainer 760, and back again. The effector arm also includes a transverse support section 1225 having a walled depression into which the microplate is received. Transverse support section 1225 prevents the well plate from slipping off of the sides of the longitudinal support section. In addition, as shown more clearly in FIG. 13, effector arm 1200 of the illustrated implementation includes one or more suction devices (e.g., including o-rings) to secure the underneath of the microplate to the effector arm during transport to and from carousel 720. Vacuum manifold 1320 and vacuum port 1330 are provided to provide suction at vacuum seal ports 1310. The underneath of the microplate is secured by the suction at ports 1310.

In the illustrated implementation, effector arm 1200 also includes a suction device (e.g., an o-ring suction device) for removing lid 1130 from microplate 1140 after it has been delivered to microplate retainer 760. The lid assists in preventing evaporation of probe material contents from the microplate wells and also helps prevent contamination of those contents during storage in carousel 720 or elsewhere. As shown more clearly in FIG. 12, de-lidding actuator 1120, under the control of executables 172, lowers vacuum suction cups 1150 onto the top of lid 1130, vacuum is applied, and actuator 1120 lifts lid 1130 off of microplate 1140.

As shown in FIG. 11, effector arm 1200 is connected to microplate transfer arm 1160 that pivots about base 1110 between carousel 720 and microplate retainer 760. Effector arm 1200 moves vertically with respect to microplate transfer arm 1160 in order to access the selected microplate slot in the selected segment of carousel 720. In the illustrated implementation, one or more sensors (represented schematically in FIG. 1 by sensors 106) are provided on effector arm 1200 to sense when maximum extension of the effector arm into the carousel has occurred. Also included on effector arm 1200 in the illustrated implementation is barcode scan engine 1420, as most clearly seen in FIG. 14 (and as schematically represented by effector arm bar code reader 112 of FIG. 1). Scan engine 1430 emits laser beams 1430 that scan a barcode affixed to microplate barcode surface 1410 of microplate 1140. In some implementations, the scanning occurs as effector arm 1200 approaches the selected slot in carousel 720 and before microplate 1140 is transferred to microplate retainer 760. If executables 172 determines that the machine-readable code (e.g., barcode in this example) identifying microplate 1140 does not include a microplate identifier that matches the identifier selected by user 101 for placement in the selected carousel slot, then executables 172 may interrupt operation of arrayer 100 and alert user 101. In this manner, probe materials are not wasted, and experiments are not compromised, due to erroneous application of probe materials to slides. In other implementations, executables 172 may determine what, if any, aspects of a spotting operation may proceed without use of the erroneously stored microplate, alert user 101, and proceed with those other aspects.

FIGS. 15A-C and 16A-C are simplified schematic representations of various views of two alternative embodiments of aspects of microplate retainer 760 illustrating fiducial features for registering bottom surfaces of the microplates to retainer 760. (See also aspects of the use of reference marks and other features and techniques as described in U.S. Pat. No. 6,121,048, hereby incorporated herein by reference in its entirety for all purposes.) FIGS. 15A-C illustrate one implementation of a cone and V-groove arrangement suitable for registering the bottom of a 96-sell microplate to retainer 760. As most clearly seen in the bottom view of FIG. 15C, certain ones of well bottoms 1550 (e.g., one or more corner well bottoms) are seated within cone features 1510 and V-groove features 1520 in this illustrative implementation. A cut-away of flat surface 1540 of retainer 760 is also shown. FIGS. 15A and 15B provide side views further illustrating these fiducial features. In some instances, the bottoms of wells may not be suitable for registering the microplate, as for example in higher density microplates in which the well bottoms are quite small, microplates in which the well bottoms are not exposed, microplates in which the well bottoms are made of a material that is too flexible to provide reliable registration, and in other instances. In these cases, registration may be accomplished, for example, by seating one or more edges of the microplate in retainer 760 using angled members. FIGS. 16A and 16C show surfaces of retainer 760 having lead-in-angles 1610 and 1620 so that microplate 1600 (in this implementation, a 384-well microplate) may be registered with respect to retainer 760 as it is lowered by robot 730 into retainer 760. Retainer 760 in this implementation is secured in a fixed location with respect to gantry system 780, as described below. In some implementations, cone and groove fiducial features of FIGS. 15A-C, or like fiducial features, may be combined with the angled-surface fiducial features shown in FIGS. 16A-C, or like fiducial features. In any of these cases, clips or other securing mechanisms (not shown) may be used to retain the microplate within retainer 760.

Having secured a microplate in retainer 760, rings of printing head 750 may be lowered into selected or predetermined microplate wells as described above. In some implementations, the ring is entirely submerged in the fluid probe material in the microplate well. In various implementations, the pin may either be kept stationery while the ring is lowered, or the tip of the pin may be positioned above the ring while both the pin and ring are lowered. As noted, given the design of the ring an amount of the fluid sample is retained within the ring by the surface tension of the fluid and the surface activity of the inner wall of the ring. After the ring is raised out of the probe material solution, the fluid held in the ring forms a convex meniscus that protrudes from the bottom opening of the ring. The ring with the sample can then be positioned at a location above a substrate (e.g., microscope slide secured on platen 740) onto which a fraction of the sample in the ring is to be deposited. The fluid volume in the ring is sufficient to deposit or spot more than one fraction. In fact, in a typical application, 100, 200, 300, 400, up to 1,000, 2,000 or more fractions can be deposited from a single fluid sample retained in the ring. In general, the number of fractions will depend on the desired volume of each fraction, the dimensions of the pin, and the viscosity of the fluid sample. Once the pin and ring mechanism of the illustrated preferred implementation is positioned over the desired location on the substrate, the tip of the pin is then lowered into, through, and out of the fluid sample retained in the ring. The surface tension of the fluid sample retains the fluid sample within the ring while the pin penetrates into and moves through and out of the fluid sample. As noted, a fraction of the fluid sample is retained on the tip of the pin. The portion of the pin that passes through the ring has a diameter that typically is small compared to the diameter of the ring, enabling the pin to pierce the fluid sample without breaking the meniscus and without causing the fluid sample to leave the ring. The pin with the sample on the tip may be lowered toward the surface of the substrate until the meniscus of the sample on the end of the pin makes initial contact with the surface of the substrate. During typical operation of the illustrative preferred embodiment, the pin contacts the substrate without damaging force. The fluid probe material then adheres via surface tension to the surface of the substrate, and as the pin is raised, the fluid probe material is transferred to the surface of the substrate by surface tension and gravity. The pin is moved back through and above the fluid probe material in the ring. The process of probe deposition may then be repeated by repositioning the pin and ring mechanism at another desired location above the surface of the substrate. Alternatively, the pin and ring may be positioned over another, different surface, e.g., moved to another microscope slide as noted above.

In the illustrated implementation, moving of printing head 750 is accomplished using a gantry system capable of moving the printing head across the length and width of the portions of platen 740 on which microscope slides may be affixed and also over microplate retainer 760. As shown in FIG. 7, print assembly 790 is positioned on an x-y gantry that includes a bar section positioned above platen 740 and on which the printing head is secured and moveable in what is referred to herein as the y direction. The bar section is secured on frame 710 and moveable in the x direction, which is orthogonal to the y direction. Movement in these directions is effectuated by gantry motors/actuators represented schematically by motors/actuators 104 of FIG. 1. During operation, the printing head may move in a serpentine manner from microscope slide to microscope slide along a column on the platen and then back along an adjacent column on the platen. However, numerous paths may be implemented, including, as noted, those in which positions on the platen are visited more than one time. Movement of the printing head along the length of the platen, i.e., what is referred to herein as the x-direction, is guided in the illustrated implementation by a series of spaced markers (represented schematically in FIG. 1 by gantry sensor system 102) engraved along the frame of the device adjacent to the platen. Movement of the printing head along the bar section, i.e. in the y-direction, is guided by a series of spaced markers (also an aspect of system 102) engraved along the bar section itself in this implementation. The printing head moves in response to a commands from executables 172 that direct sensors to count markers and arrive at a preprogrammed destination. However, these techniques for moving in the x or y directions in an accurate and controlled manner are illustrative only, and various other techniques known to those skilled in the relevant art may be used in other implementations. For example, mechanisms to control movement in the x and y directions are known to those of skill in the art and are shown in U.S. Pat. No. 6,121,048, incorporated by reference above. Various aspects of producing probe arrays and related operations are also described in U.S. Pat. No. 6,269,846, incorporated by reference above, and in U.S. Pat. Nos. 6,329,143; 6,309,831; 6,271,957; 6,261,776; 6,239,273; 6,238,862; 6,156,501; 6,150,147; 6,136,269; 6,121,048; 6,040,193; 5,885,837; 5,837,832; 5,831,070; 5,770,722; 5,744,305; 5,677,195; 5,599,695; 5,583,211; 5,554,501; 5,491,074; 5,482,867; 5,429,807; and 5,384,261, all of which are hereby incorporated herein in their entireties for all purposes.

Figure 17:
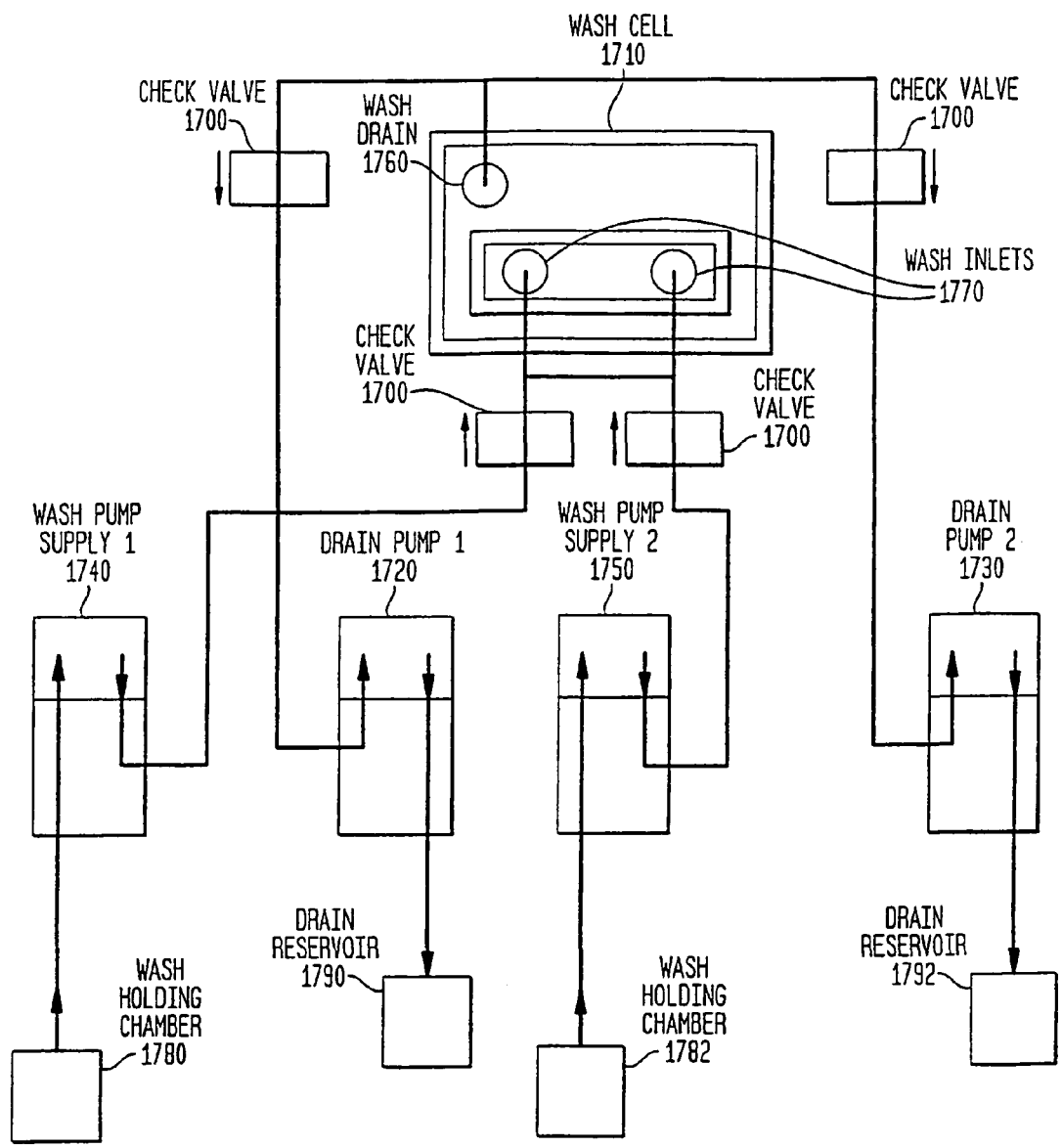
FIG. 17 is a simplified schematic representation of one embodiment of a washing system for washing spotting mechanisms of the arrayer of FIG. 7.
Figure 18:
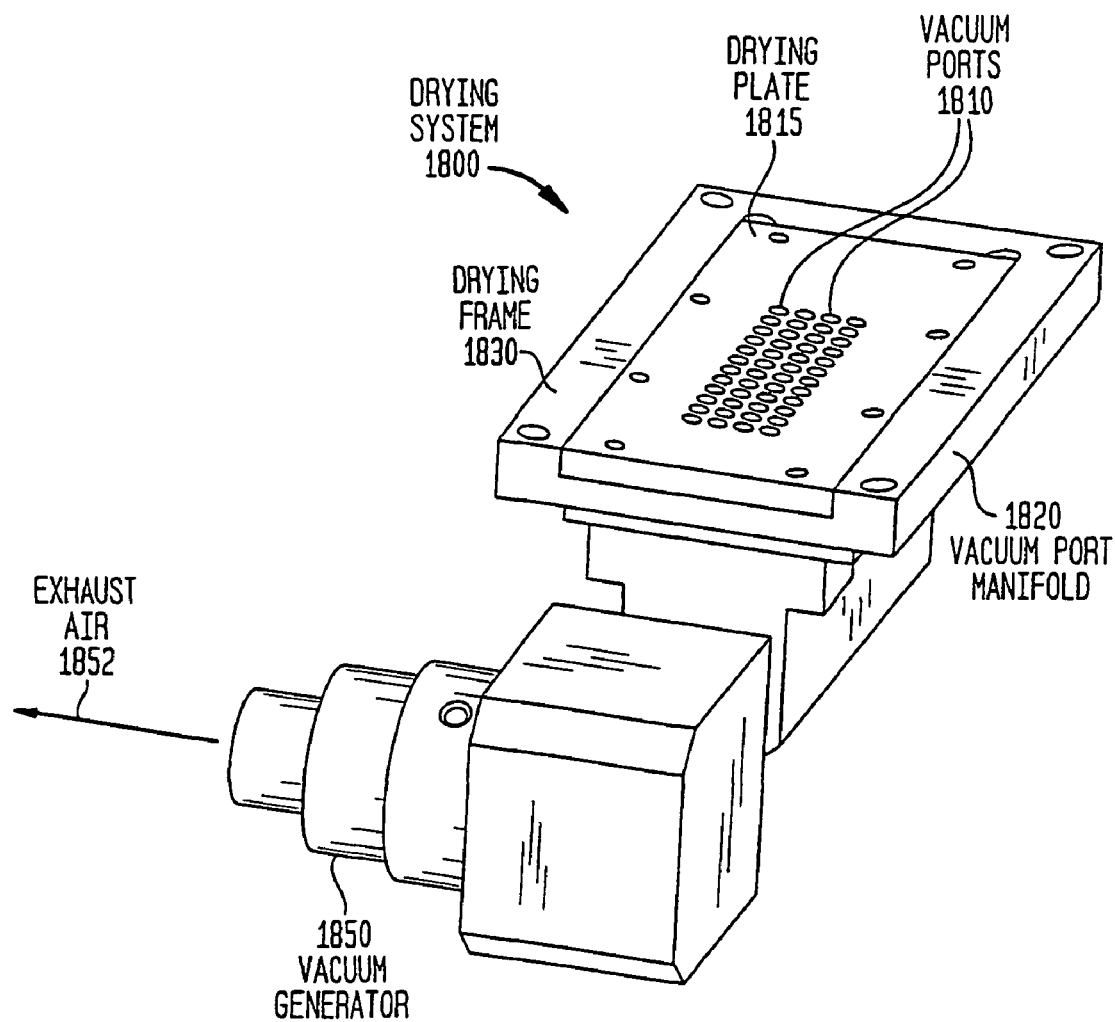
FIG. 18 is a simplified schematic representation of one embodiment of a drying system that may be used in connection with the washing system of FIG. 17.

As illustrated in FIGS. 17 and 18, the arrayer of the illustrative embodiment is designed to wash and dry the pins and rings to prevent contamination of probe material in the well plates and on the microscope slides. In the preferred implementation illustrated herein, the printing head has the option of utilizing a separate wash station (e.g., wash station 735 shown in FIG. 7) and a separate dry station to clean the pins and rings between spotting applications. As shown schematically in FIG. 17, a wash cell 1710 in wash station 736 is flooded with wash solution by wash pumps 1740 and 1750 through wash inlets 1770. In this implementation, there are two inlets 1770 to which piping is connected so that liquids from separate wash holding chambers 1780 and 1782 may be pumped, via check valves 1700, into wash cell 1710. The wash station also includes, in this implementation, two drain reservoirs 1790 and 1792. Multiple drains, typically coupled to multiple pumps such as drain pumps 1720 and 1730, may be used to provide that different solutions are drained, via wash drain 1760 and check valves 1700, into different drain reservoirs 1790 and 1792. Use of multiple drain paths and drain reservoirs provides the advantage that solutions may be used again and also may be advantageous to avoid dangerous mixing of solutions. In some implementations, one wash pump may be on while the other is off so that sequential washing takes place, potentially using two different liquids. In other implementations, both wash pumps may be on at the same time so that the two liquids are injected together into the washing cell. Also, in other implementations, a "Y" coupling or similar arrangement or manifold may be provided so that more than two liquids from separate holding chambers may be sequentially or simultaneously, in any combination, pumped or otherwise provided to the washing station.

In an illustrative washing operation, the pins and rings are lowered into the washing chamber and then raised out of the washing chamber. The pins and rings are then lowered, in accordance with this implementation, into a separate drying chamber that uses compressed air or vacuum to generate suction thereby removing fluid from the pins and rings. The drying station may be situated in proximity to the washing chamber, or at any other location accessible by gantry system 780. FIG. 18 is a simplified representation of a drying system 1800 suitable for drying pins and rings. As shown in the illustrative implementation of FIG. 18, one of vacuum ports 1810 is provided for each pin and ring, and the ports are arranged in a pattern in drying plate 1815 in order to match the pattern of pins and rings being used with printing head 750. Plate 1815 is removable in this implementation from drying frame 1830, within which is provided vacuum port manifold 1820, so that alternative patterns of vacuum ports may be employed that are suitable for use with other patterns of pins and rings. Vacuum generator 1850, which may for example be an air amplifier type vacuum generator, provides the vacuum. Air is exhausted from generator 1850 as indicated by exhaust arrow 1852. The various wash and dry pumps and valve actuators and motors may be employed in numerous configurations as will be appreciated by those of ordinary skill in the relevant art, and these various implementations are represented schematically by actuators/motors 118 of FIG. 1. Related sensors, which may be applied in accordance with techniques known to those of ordinary skill in the relevant art, are represented by sensors 120 of FIG. 1.

An alternative washing and drying system is described in PCT Application PCT/US01/04285 (Publication Number WO 01/58593), which is incorporated by reference above.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on, may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and "local" to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A spotting system, comprising:
   a microplate holder constructed and arranged to hold a plurality of microplates;
   a microplate handling apparatus constructed and arranged to retrieve from the microplate holder a first microplate having a plurality of wells;
   at least one depositing element, including a pin and a ring, constructed and arranged to receive biological material from the first microplate by dipping into the well of the microplate and to deposit the biological material on one or more substrates;

a cleaning apparatus constructed and arranged to wash a depositing element after it has deposited the biological material; and a computer system including a processor, a display and a memory unit, the memory unit having stored therein executable computer program instructions that, when executed by the processor, provide one or more graphical user interfaces constructed and arranged to (a) present a user with an option to select the first microplate, (b) present the user with an option to associate at least one probe material with one or more of the plurality of wells of the first microplate, and (c) present the user with an option to associate one or more locations on the one or more substrates with the one or more wells.

2. An arrayer system, comprising:

a microplate handling apparatus including a microplate holder constructed and arranged to hold a plurality of microplates each including a plurality of wells;

a print head including at least two pins constructed and arranged for deposition of biological material from the wells to a substrate to form a probe array, and a computer system including a processor, a display and a memory unit, the memory unit having stored therein executable computer program instructions to provide a graphical user interface for controlling operation of the print head, the graphical user interface being constructed and arranged to provide on said display two or more windows comprising:

a first window providing data features about the print head including positional information about the pins constructed to deposit a probe array using the biological material, a second window providing a probe list associated with the microplate;

the memory unit further including computer program instructions that, when executed by the processor, perform a method comprising the steps of (a) selecting a first microplate having a plurality of wells, (b) associating at least one probe material with one or more of the wells, and (c) associating one or more locations on one or more substrates with the one or more wells for deposition of the probes on the substrates using the print head.

3. The system of claim 2, wherein:

the first microplate is held by the microplate handling apparatus.

4. The system of claim 2, wherein:

the microplate handling apparatus further includes an effector that retrieves, under control of the computer, the first microplate from the microplate holder.

5. An arrayer system, comprising:

a microplate handling apparatus including a microplate holder constructed and arranged to hold a plurality of microplates each including a plurality of wells;

a print head including at least two pins constructed and arranged for deposition of biological material from the wells to a substrate, and a computer system including a processor, a display and a memory unit, the memory unit having stored therein executable computer program instructions that, when executed by the processor, provide one or more graphical user interfaces constructed and arranged to provide at least two windows designed to (a) present a user with an option to select a first microplate having a plurality of wells, (b) present the user with an option to associate at least one probe material with one or more of the wells, and (c) present the user with an option to associate one or more locations on one or more substrates with the one or more wells, the graphical user interface also correlating positional information regarding the pins, for designing a specific pattern of probes to be deposited on the substrate using the corresponding biological material.

6. The system of claim 2 or 5, wherein:

one of the windows displays a simulated substrate together with the positional information about the pins.

7. The system of claim 2 or 5, wherein:

one of the windows is a replicate positions window for specifying locations of probes to be replicated on the substrate.

8. The system of claim 2 or 5, wherein:

one of the windows enables selection of a microplate from the plurality of microplates.

9. The system of claim 2 or 5, wherein:

one of the windows is a microplate identifier window for representing a selected microplate.

10. The system of claim 9, wherein the graphical user interface provides a dialog box for naming a microplate associated with the microplate identifier window.

11. The system of claim 2 or 5, wherein:

one of the windows is a source probe list window.

12. The system of claim 5, wherein:

one of the windows is a microplate probe list window.

13. The system of claim 2 or 5, wherein the graphical user interface is arranged to enable a user to select probes from a source probe list window and add or remove them from a microplate probe list window.

14. The system of claim 2, wherein:

one of the windows is a microplate well display window.

15. The system of claim 14, wherein the microplate well display window shows an illustrative configuration of wells in a selected microplate.

16. The system of claim 2 or 5, wherein:

one of the windows is a microplate well list window.

17. The system of claim 16, wherein the microplate well list window provides genomic information related to a probe.

18. The system of claim 16, wherein the microplate well list window provides genomic information related to a probe associated with a selected well of a microplate displayed in a microplate well display window.

19. The system of claim 2 or 5, wherein:

the biological material is selected from the group including a ligand, receptor, protein, protein fragment, peptide, nucleic acid (oligonucleotide or polynucleotide of RNA or DNA), antibody, small molecule, or other biological molecule.

20. The system of claim 2 or 5 including a bar code reader constructed and arranged to scan a bar code on a surface associated with a microplate.

21. The system of claim 2 or 5 including a microplate retainer includes one or more fiducial features for receiving a radius of microplate well bottoms so as to register the selected microplate with respect to the microplate retainer.

22. The system of claim 18, wherein:

the one or more fiducial features include at least one cone and groove fiducial feature.

23. The system of claim 1, wherein:

the plurality of wells adapted and constructed to hold probe material selected from the group including a ligand, receptor, protein, protein fragment, peptide, nucleic acid (oligonucleotide or polynucleotide of RNA or DNA), antibody, small molecule, or other biological molecule.

24. The system of claim 1 including a bar code reader constructed and arranged to scan a bar code on a surface associated with a microplate.

25. The system of claim 1 wherein the microplate handling apparatus includes microplate retainer that comprises one or more fiducial features for receiving a radius of microplate well bottoms so as to register a microplate with respect to the microplate retainer.

26. The system of claim 25, wherein:
the one or more fiducial features include at least one cone and groove fiducial feature.

* * * * *